United States Patent
Kubota et al.

(10) Patent No.: US 8,404,619 B2
(45) Date of Patent: Mar. 26, 2013

(54) PARTICULATE PLANT TREATMENT COMPOSITION

(75) Inventors: Naoki Kubota, Hyogo (JP); Nobuhiro Taniguchi, Hyogo (JP); Hisakazu Hojo, Hyogo (JP)

(73) Assignee: Maruo Calcium Company Limited, Akashi-shi (JP)

( * ) Notice: Subject to any disclaimer, the term of this patent is extended or adjusted under 35 U.S.C. 154(b) by 1344 days.

(21) Appl. No.: 11/884,789

(22) PCT Filed: Feb. 20, 2006

(86) PCT No.: PCT/JP2006/302953
§ 371 (c)(1),
(2), (4) Date: Aug. 21, 2007

(87) PCT Pub. No.: WO2006/090666
PCT Pub. Date: Aug. 31, 2006

(65) Prior Publication Data
US 2008/0153703 A1   Jun. 26, 2008

(30) Foreign Application Priority Data
Feb. 22, 2005 (JP) ................. 2005-045332

(51) Int. Cl.
*A01N 59/00* (2006.01)
*A01N 25/00* (2006.01)
(52) U.S. Cl. .................... 504/125; 71/64.13
(58) Field of Classification Search .............. 504/125
See application file for complete search history.

(56) References Cited

U.S. PATENT DOCUMENTS

| 6,391,079 | B1 * | 5/2002 | Takeda et al. ................ 71/27 |
| 2004/0233430 | A1 * | 11/2004 | Jorgensen et al. ........... 356/337 |
| 2005/0245396 | A1 * | 11/2005 | Hojo et al. ................ 504/116.1 |

FOREIGN PATENT DOCUMENTS

| JP | 34-6214 | 7/1959 |
| JP | 58-223681 | 12/1983 |
| JP | 61-36188 | 2/1986 |
| JP | 10-001384 | 1/1998 |
| JP | 2000-026185 | 1/2000 |
| JP | 2001-190154 | 7/2001 |
| WO | WO 2004012507 A1 * | 2/2004 |

OTHER PUBLICATIONS

International Search Report dated Apr. 4, 2006.

* cited by examiner

*Primary Examiner* — Fereydoun G Sajjadi
*Assistant Examiner* — Michael B Pallay
(74) *Attorney, Agent, or Firm* — Kratz, Quintos & Hanson, LLP

(57) ABSTRACT

A sparingly water-soluble plant quality improver characterized by containing a polyvalent metal, an organic acid having a carboxylic group, an alkali metal and/or ammonia, and phosphate ions and/or carbonate ions. The sparingly water-soluble plant quality improver inhibits or alleviates physiological disorders of plants and further has the function of improving qualities of the plants, such as sugar content and acidity. It is also characterized in that it causes little fruit surface soiling to heighten the merchandice value, and that it is lowly phytotoxic and highly safe.

7 Claims, No Drawings

PARTICULATE PLANT TREATMENT COMPOSITION

TECHNICAL FIELD

The present invention relates to a sparingly water-soluble plant quality improver for use as a leaf application to plants for inhibiting or alleviating physiological disorders of the plants.

BACKGROUND ART

It is known that various disorders are caused by various mineral deficiencies in plants such as fruit trees, fruit vegetables, leaf vegetables, and root vegetables. Examples of disorders caused by a calcium deficiency include bitter pit in apples, peel puffing in citrus fruits, blossom-end rot in tomatoes or bell peppers, fermented or deformed fruits in melons or water melons, tip burn in strawberries, blackheart in lettuces or celery cabbages, and burned tip in flowering plants. On the other hand, magnesium is an essential element required in large quantities by plants and is also a central element of a chlorophyll composition. Magnesium deficiency reduces photosynthesis, and therefore reduces the growth of plants. Furthermore, when a plant is cultivated on alkali soil, iron deficiency is likely to develop and leads to various disorders.

Calcium is an essential nutrient for plants because it is, for example, a component of cell walls of plants. In recent years, however, acidification of soil is likely to occur due to an effect of acid rain and the like, and this situation would be extremely likely to cause a symptom of calcium deficiency in plants. In order to solve this problem, a method for fertilizing soil with calcium is provided. However, calcium is a nutrient whose rate of transport within a plant is very slow, and therefore it is difficult to obtain an effect of calcium fertilization immediately after fertilizing soil when a symptom of calcium deficiency develops in a specific part of the plant. In order to solve this problem, a method of spraying a calcium preparation and the like onto a leaf surface and the like has been taken so as to allow calcium and the like to be absorbed directly into a nutrient-deficient part of the plant.

Water-soluble calcium, such as calcium chloride and calcium nitrate, is conventionally used as a leaf application. However, these calcium preparations have a problem that their counter ions such as chlorine ions and nitrate ions will cause phytotoxicity. In order to avoid this problem of phytotoxicity, it has been proposed to use a water-soluble calcium preparation containing, for example, calcium formate as an active ingredient (for example, Patent Document 1). This method can solve the problem of phytotoxicity due to the counter ions, however, absorption of calcium is far from sufficiency. That is, it is not necessarily effective for resolution of bitter pit in apples, for example.

Furthermore, it has been proposed to use a water-soluble solid preparation containing calcium carbonate and one or more organic acids selected from the group consisting of citric acid, malic acid, tartaric acid, gluconic acid, succinic acid, malonic acid, glutaric acid, maleic acid, fumaric acid and glutaconic acid (for example, Patent Document 2). In this method, calcium carbonate solubilized in water with the help of various organic acids is used as a source of calcium in order to solve the problem of phytotoxicity due to the counter ions such as calcium chloride. In this method, however, calcium carbonate is used in a form of an aqueous solution having an acidic pH of, for example, pH 1.5. Therefore, there is a problem that fruit or leaf burn caused by acid is likely to occur and acidification of soil is also likely to occur. This method, therefore, is not necessarily preferred.

It has been proposed to use a preparation formulated with 5 to 40 wt % of water-soluble calcium salts and 1 to 10% of a spreading organic polymer, based on calcium carbonate having a particle diameter of not less than 0.6 μm and not more than 2.8 μm, as a quality improver for fruits (for example, Patent Document 3). In the case of this method, calcium carbonate and water-soluble calcium salts are suspended in water to be used as the preparation. However, a specific gravity of calcium carbonate is as large as 2.7, and the resulting preparation is not necessarily in a good dispersion state. Therefore, there is a problem that suspended solids in water are likely to precipitate at a bottom of a container. In the case of using this preparation, an effect of preventing peel puffing is likely to be non-uniform and is far from sufficiency due to the above problem. Further, using this preparation, there is also a problem that a surface of a fruit is soiled whitish due to mainly coarse particles and secondary aggregates of calcium carbonate and the like, which are generated by spraying the preparation and evaporating to dryness. Therefore, there is a problem that much work is needed to wipe off the whitish dirt.

It has been proposed to use a calcium fertilizer for leaf application containing a highly soluble calcium salt and a poorly soluble calcium salt in a ratio of 10 to 50%:90 to 50% (for example, Patent Document 4). According to this method, phytotoxicity can be reduced by using a fertilizer containing a highly soluble calcium salt and a poorly soluble calcium salt in a predetermined ratio. However, a counter ion responsible for the phytotoxicity is present in a certain quantity in the fertilizer and therefore, a problem of the phytotoxicity is far from being completely solved. Further, this method is far from being fully effective, as in the method described in Patent Document 1, to overcome a physiological disorder such as bitter pit, since this is only a method of spraying a calcium preparation having a low possibility of causing the phytotoxicity. Although this method provides a certain level of effect for preventing peel puffing, it is also far from being fully effective as in the method described in Patent Document 1. There is also a drawback that the calcium preparation cannot be used in combination with a phosphate fertilizer, since they would react with each other.

There has been proposed a method for preventing apple flesh browning during cold storage. This method includes applying, to a surface of an apple, a suspension which contains calcium phosphate having a particle size of not more than 10 μm and a molar ratio of Ca/P in the range of 0.8 to 1.5 (for example, Patent Document 5). In this method, the particle size is reduced using a grinding machine. However, there is a limitation in the reduction of the particle size, and the remaining coarse particles without being ground cannot contribute to producing the desired effect. Therefore, it is difficult to obtain a sufficient effect in this method.

In the case of using a magnesium preparation, on the other hand, there is the same problem as with a calcium preparation. That is, the use of a water-soluble magnesium preparation such as magnesium chloride, magnesium nitrate and magnesium sulfate is not preferable since counter ions such as chlorine ions, nitrate ions and sulfate ions causes phytotoxicity.

In order to solve this problem, a magnesium fertilizer containing magnesium acetate has been proposed (for example, Patent Document 6). According to this method, the phytotoxicity can be reduced. However, the spraying effect is far from sufficiency, as with the calcium preparation, by merely spraying an aqueous solution of the magnesium preparation. In addition, there is a drawback that the effect of a water-soluble magnesium preparation is likely to be affected by the weather, since the preparation would easily run off by rain.

As an iron preparation, on the other hand, organic chelated iron has been used for leaf application or soil application. However, organic chelated iron is expensive and the reality is that the adoption rate is very low.

Patent Document 1: Japanese Examined Patent Publication No. S62-28117

Patent Document 2: Japanese Unexamined Patent Publication No. 2004-238248

Patent Document 3: Japanese Examined Patent Publication No. S59-19923

Patent Document 4: Japanese Patent No. 2563067

Patent Document 5: Japanese Examined Patent Publication No. H2-33349

Patent Document 6: Japanese Unexamined Patent Publication No. H6-172069

DISCLOSURE OF THE INVENTION

Problems to be Solved by the Invention

In view of the above circumstances, the present invention relates to a plant quality improver for solving the above problems. More specifically, the present invention aims to provide a sparingly water-soluble plant quality improver for leaf application which can produce the following effects of preventing peel puffing in citrus fruits, reducing physiological disorders such as bitter pit in apples, water core in pears, cherries, etc., and fruit-cracking in fruit vegetables, reducing organic acids and increasing sugar content in fruits, or the like.

Means for Solving the Problems

The present invention is, in a first aspect, to provide a sparingly water-soluble plant quality improver characterized by containing a polyvalent metal, an organic acid having a carboxylic group, an alkali metal and/or ammonia, and phosphate ions and/or carbonate ions.

The present invention is, in a second aspect, to provide a sparingly water-soluble plant quality improver containing a polyvalent metal, an organic acid having a carboxylic group, an alkali metal and/or ammonia, and phosphate ions and/or carbonate ions, which is prepared by a process selected from the following (I) to (IV):

(I) A process of preparing a precursor by mixing water, a polyvalent metal compound, an organic acid having a carboxylic group, and an alkali metal source and/or an ammonia source, and adding to the precursor a phosphoric acid source and/or a carbonic acid source;

(II) A process of preparing a precursor by mixing water, a polyvalent metal compound, a phosphoric acid source and/or a carbonic acid source, and an alkali metal source and/or an ammonia source, and adding to the precursor an organic acid having a carboxylic group;

(III) A process of preparing a precursor by mixing water, a polyvalent metal compound and an organic acid having a carboxylic group, and adding to the precursor a phosphoric acid source and an alkali metal source and/or an ammonia source, and/or a carbonic acid source and an alkali metal source and/or an ammonia source; and (IV) A process of preparing a precursor by mixing water, a polyvalent metal compound, an organic acid having a carboxylic group, and a phosphoric acid source and/or a carbonic acid source, and adding to the precursor an alkali metal source and/or an ammonia source.

The present invention is, in a third aspect, to provide a process for producing a sparingly water-soluble plant quality improver containing a polyvalent metal, an organic acid having a carboxylic group, an alkali metal and/or ammonia, and phosphate ions and/or carbonate ions, which comprises a process selected from the following (I) to (IV):

(I) A process of preparing a precursor by mixing water, a polyvalent metal compound, an organic acid having a carboxylic group, and an alkali metal source and/or an ammonia source, and adding to the precursor a phosphoric acid source and/or a carbonic acid source;

(II) A process of preparing a precursor by mixing water, a polyvalent metal compound, a phosphoric acid source and/or a carbonic acid source, and an alkali metal source and/or an ammonia source, and adding to the precursor an organic acid having a carboxylic group;

(III) A process of preparing a precursor by mixing water, a polyvalent metal compound and an organic acid having a carboxylic group, and adding to the precursor a phosphoric acid source and an alkali metal source and/or an ammonia source, and/or a carbonic acid source and an alkali metal source and/or an ammonia source; and (IV) A process of preparing a precursor by mixing water, a polyvalent metal compound, an organic acid having a carboxylic group, and a phosphoric acid source and/or a carbonic acid source, and adding to the precursor an alkali metal source and/or an ammonia source.

Effects of the Invention

A sparingly water-soluble quality improver of the present invention has a fine and uniform particle size and therefore, when sprayed on a plant, it is absorbed very efficiently through the stomata of the plant. Further, the sparingly water-soluble quality improver of the present invention is less likely to cause phytotoxicity and less affected by the weather as compared with a water-soluble chemical. In addition, the quality improver can be used in combination with a water-soluble phosphate fertilizer. The sparingly water-soluble quality improver of the present invention is so highly redispersible in water that it is dispersed easily in water without using a specific dispersing machine, a specific stirrer, etc., and therefore it has a constant quality-improving effect. In addition, the quality improver does not precipitate in a spreader, and therefore the quality improver is not likely to cause problems such as device failure, clogging and rusting of a sprayer, etc., which are caused by a commonly used sparingly water-soluble chemical.

BEST MODES FOR CARRYING OUT THE INVENTION

As used in the present invention, "a polyvalent metal compound" refers to a divalent or trivalent metal compound and includes, for example, calcium hydroxide, magnesium hydroxide, iron hydroxide, calcium oxide, magnesium oxide, iron oxide, calcium chloride, magnesium chloride, iron chloride, calcium carbonate, magnesium carbonate, iron carbonate, calcium nitrate, magnesium nitrate, iron nitrate, calcium sulfate, magnesium sulfate, iron sulfate, calcium phosphate, magnesium phosphate, iron phosphate, ferric pyrophosphate, and dolomite, which may be used alone or, if necessary, two or more of them may be used in combination. In order to obtain a more effective sparingly water-soluble quality improver, the polyvalent metal compound used herein is preferably at least one selected from calcium hydroxide, magnesium hydroxide, iron hydroxide, calcium oxide, magnesium oxide, iron oxide, magnesium carbonate, calcium carbonate, iron carbonate, dolomite and ferric chloride, and most preferably at least one selected from calcium hydroxide, calcium oxide and calcium carbonate.

As used in the present invention, "an organic acid having a carboxylic group" includes, for example, malic acid, succinic acid, citric acid, adipic acid, fumaric acid, glutamic acid, gluconic acid, and an alkali metal salt, an ammonium salt and a polyvalent metal salt thereof, which may be used alone or, if necessary, two or more of them may be used in combination. In order to obtain a more effective sparingly water-soluble quality improver, the organic acid having a carboxylic group used herein is preferably at least one selected from citric acid, potassium citrate, sodium citrate, calcium citrate, magnesium citrate, ferric ammonium citrate, iron citrate and sodium ferrous citrate.

As used in the present invention, "a phosphoric acid source" includes, for example, phosphoric acid, a condensed phosphoric acid, an alkali metal salt of phosphoric acid, and an ammonium salt of phosphoric acid, which may be used alone or, if necessary, two or more of them may be used in combination. Examples of condensed phosphoric acids may include sodium tripolyphosphate, sodium tetrapolyphosphate, sodium pentapolyphosphate, sodium hexametaphosphate, ultraporin, potassium tripolyphosphate, potassium tetrapolyphosphate, potassium pentapolyphosphate, and potassium hexametaphosphate. Examples of alkali metal salts of phosphoric acid may include monosodium phosphate, disodium phosphate, trisodium phosphate, monopotassium phosphate, dipotassium phosphate, and tripotassium phosphate. Examples of ammonium salts of phosphoric acid may include monoammonium phosphate and diammonium phosphate. They may be used alone, or two or more of them may be used in combination.

As used in the present invention, "a carbonic acid source" includes, for example, carbonic acid, an alkali metal salt of carbonic acid, an ammonium salt of carbonic acid, and urea, which may be used alone or, if necessary, two or more of them may be used in combination. Examples of alkali metal salts of carbonic acid may include sodium carbonate, sodium hydrogen carbonate, potassium carbonate, and potassium bicarbonate. Examples of ammonium salts of carbonic acid may include monoammonium carbonate and diammonium carbonate. They may be used alone, or two or more of them may be used in combination.

As used in the present invention, "a phosphoric acid source and an alkali metal source and/or an ammonia source" refers to an alkali metal phosphate, an alkali metal condensed phosphate, a mixture of phosphoric acid and an alkali metal, a mixture of an alkali metal phosphate and an alkali metal, an ammonium salt of phosphoric acid, an ammonium salt of condensed phosphoric acid, a mixture of phosphoric acid and an ammonia source, a mixture of an ammonium salt of phosphoric acid and an ammonia source, a mixture of an ammonium salt of phosphoric acid and an alkali metal, a mixture of an alkali metal condensed phosphate and an alkali metal, and the like. More specifically, examples of alkali metal phosphates may include monosodium phosphate, disodium phosphate, trisodium phosphate, monopotassium phosphate, dipotassium phosphate, and tripotassium phosphate. Examples of alkali metal condensed phosphates may include sodium tripolyphosphate, sodium tetrapolyphosphate, sodium pentapolyphosphate, sodium hexametaphosphate, ultraporin, potassium tripolyphosphate, potassium tetrapolyphosphate, potassium pentapolyphosphate, and potassium hexametaphosphate. Examples of mixtures of phosphoric acid and an alkali metal may include a mixture of phosphoric acid and at least one selected from alkali metal sources such as sodium hydroxide, sodium oxide, sodium chloride, sodium nitrate, potassium hydroxide, potassium oxide, potassium chloride, and potassium nitrate. Examples of mixtures of an alkali metal phosphate and an alkali metal may include a mixture of the above alkali metal phosphate and at least one selected from alkali metal sources such as sodium hydroxide, sodium oxide, sodium chloride, sodium nitrate, potassium hydroxide, potassium oxide, potassium chloride, and potassium nitrate. Examples of ammonium salts of phosphoric acid may include ammonium phosphates such as monoammonium phosphate and diammonium phosphate. Examples of ammonium salts of condensed phosphoric acid may include an ammonium salt of the above condensed phosphoric acid. Examples of mixtures of phosphoric acid and an ammonia source may include a mixture of phosphoric acid and at least one selected from ammonia, aqueous ammonia, ammonium nitrate, ammonium chloride, ammonium sulfate, ammonium hydrogen sulfate and the like. Examples of mixtures of an ammonium salt of phosphoric acid and an ammonia source may include a mixture of the above ammonium salt of phosphoric acid and at least one selected from ammonia sources. Examples of mixtures of an ammonium salt of phosphoric acid and an alkali metal may include a mixture of monoammonium phosphate, diammonium phosphate the or the like and at least one selected from alkali metal sources such as sodium hydroxide, sodium oxide, sodium chloride, sodium nitrate, potassium hydroxide, potassium oxide, potassium chloride, and potassium nitrate. Examples of mixtures of an alkali metal condensed phosphate and an alkali metal may include a mixture of the above alkali metal condensed phosphate and at least one selected from alkali metal sources such as sodium hydroxide, sodium oxide, sodium chloride, sodium nitrate, potassium hydroxide, potassium oxide, potassium chloride, and potassium nitrate. They may be used alone, or two or more of them may be used in combination.

As used in the present invention, "a carbonic acid source and an alkali metal source and/or an ammonia source" refers to an alkali metal carbonate, a mixture of carbonic acid and an alkali metal, a mixture of an alkali metal carbonate and an alkali metal, an ammonium salt of carbonic acid, a mixture of carbonic acid and an ammonia source, a mixture of an ammonium salt of carbonic acid and an ammonia source, a mixture of an ammonium salt of carbonic acid and an alkali metal, a mixture of urea and an alkali metal, a mixture of urea and an ammonia source, and the like. More specifically, examples of alkali metal carbonates may include sodium carbonate, sodium hydrogen carbonate, potassium carbonate, and potassium bicarbonate. Examples of mixtures of carbonic acid and an alkali metal include a mixture of carbonic acid and at least one selected from alkali metal sources such as sodium hydroxide, sodium oxide, sodium chloride, sodium nitrate, potassium hydroxide, potassium oxide, potassium chloride, and potassium nitrate. Examples of mixtures of an alkali metal carbonate and an alkali metal include a mixture of the above-exemplified alkali metal carbonate and at least one selected from alkali metal sources such as sodium hydroxide, sodium oxide, sodium chloride, sodium nitrate, potassium hydroxide, potassium oxide, potassium chloride, and potassium nitrate. Examples of ammonium salts of carbonic acid may include ammonium hydrogen carbonate and ammonium carbonate. Examples of mixtures of carbonic acid and an ammonia source may include a mixture of carbonic acid and at least one selected from ammonia, aqueous ammonia, ammonium nitrate, ammonium chloride, ammonium sulfate, ammonium hydrogen sulfate and the like. Examples of mixtures of an ammonium salt of carbonic acid and an ammonia source may include a mixture of the above ammonium salt of carbonic acid and at least one selected from ammonia sources. Examples of mixtures of an ammonium salt of carbonic acid and an alkali metal may include a mixture of an ammonium salt of carbonic acid, such as ammonium carbonate and ammonium hydrogen carbonate, and at least one selected from alkali metal sources such as sodium hydroxide, sodium oxide, sodium chloride, sodium nitrate, potassium hydroxide, potassium oxide, potassium chloride, and potassium nitrate. Examples of mixtures of urea and an alkali metal may include a mixture of urea and at least one selected from alkali metal sources such as sodium hydroxide, sodium oxide, sodium chloride, sodium nitrate, potassium hydroxide, potassium oxide, potassium chloride, and potassium nitrate. Examples of mixtures of urea and an ammonia source may include a mixture of urea and at least one selected from the above ammonia sources. They may be used alone, or two or more of them may be used in combination.

As used in the present invention, "an alkali metal source and/or an ammonia source" includes, for example, sodium hydroxide, potassium hydroxide, sodium oxide, potassium oxide, sodium chloride, potassium chloride, sodium nitrate, potassium nitrate, ammonia, aqueous ammonia, ammonium sulfate, ammonium hydrogen sulfate, ammonium nitrate and ammonium chloride, as well as an alkali metal salt and/or an ammonium salt of the above organic acid having a carboxylic group, an alkali metal salt and/or an ammonium salt of phosphoric acid, and an alkali metal salt and/or an ammonium salt of carbonic acid. They may be used alone, or two or more of them may be used in combination.

It is preferable to adjust a molar ratio of each component of the sparingly water-soluble quality improver of the present invention as follows. That is, the molar ratio of polyvalent metal ions to organic acid having a carboxylic group ions is preferably ranged from 0.1 to 200, and more preferably from 0.2 to 100, and even more preferably from 0.2 to 50, in order to obtain a better effect.

The molar ratio of polyvalent metal ions to alkali metal ions and/or ammonium ions is preferably ranged from 0.03 to 200, and more preferably from 0.06 to 100, and even more preferably from 0.06 to 50, in order to obtain a better effect.

When an alkali metal salt and/or an ammonium salt of organic acid having a carboxylic group, an alkali metal salt and/or an ammonium salt of phosphoric acid, an alkali metal salt and/or an ammonium salt of carbonic acid, and the like are used as a raw material, the molar ratio thereof is calculated on the basis of an amount of ammonium salts contained in the alkali metal salt and/or the ammonium salt of organic acid having a carboxylic group, the alkali metal salt and/or the ammonium salt of phosphoric acid, and the alkali metal salt and/or the ammonium salt of carbonic acid, even though they are not particularly indicated as an alkali metal salt and/or an ammonium salt.

The molar ratio of polyvalent metal ions to phosphate ions is preferably ranged from 1 to 10, and more preferably from 1.2 to 5, even more preferably from 1.3 to 3, and most preferably from 1.5 to 1.7, in order to obtain a better effect.

The molar ratio of polyvalent metal ions to carbonate ions is preferably ranged from 0.6 to 10, and more preferably from 0.7 to 5, even more preferably from 0.7 to 3, and most preferably from 0.8 to 1.2, in order to obtain a better effect.

When both phosphate ions and carbonate ions are used, the molar ratio to the above polyvalent metal ions may be calculated as total moles of the phosphate ions and the carbonate ions. The molar ratio of polyvalent metal ions to phosphate ions and carbonate ions is preferably ranged from 0.7 to 10, and more preferably from 0.8 to 5, and even more preferably from 0.8 to 3, in order to obtain a better effect.

When the molar ratio of polyvalent metal ions to organic acid ions is less than 0.1, the percentage of a sparingly water-soluble substance in the sparingly water-soluble quality improver decreases. As a result, not only stable effects can not be obtained, but also the cost goes up, and therefore it is not preferable. When the molar ratio exceeds 200, the dispersion state of the sparingly water-soluble quality improver tends to be unstable, and therefore it is not preferable.

When the molar ratio of polyvalent metal ions to alkali metal ions and/or ammonium ions is less than 0.03, excess alkali metal salts and/or ammonium salts may affect plants, and therefore it is not preferable. When the molar ratio exceeds 200, on the other hand, the dispersion state of the sparingly water-soluble quality improver tends to be unstable. As a result, a large amount of aggregate of polyvalent metal salts is likely to precipitate at a bottom of a container such as a sprayer, in the form of inorganic salts. Therefore, it is not preferable.

When the molar ratio of polyvalent metal ions to phosphate ions is less than 1, the acidity tends to be too high and there is an increasing possibility to cause phytotoxicity on plants, and therefore it is not preferable. When the molar ratio exceeds 10, on the other hand, a crystallinity of the sparingly water-soluble quality improver tends to be unstable, and therefore it is not preferable. When the molar ratio of polyvalent metal ions to carbonate ions is less than 0.6, the acidity tends to be too high and there is an increasing possibility to cause phytotoxicity on plants, and therefore it is not preferable. When the molar ratio exceeds 10, on the other hand, a dispersion stability of the sparingly water-soluble quality improver tends to be unstable, and therefore it is not preferable.

When the molar ratio of polyvalent metal ions to phosphate ions and carbonate ions is less than 0.7, the acidity becomes so high that there is a possibility to cause phytotoxicity on plants. Therefore, it is not preferable. When the molar ratio exceeds 10, on the other hand, a reaction becomes unstable and coarse particles are likely to be present in the sparingly water-soluble quality improver. Therefore, it is not preferable since it becomes difficult to obtain a stable effect.

The sparingly water-soluble plant quality improver of the present invention is produced by adding water, a polyvalent metal compound, an organic acid having a carboxylic group, an alkali metal source and/or an ammonia source, and a phosphoric acid source and/or a carbonic acid source to thereby prepare a mixed slurry. The mixing process is broadly divided into the following processes (I), (II), (III), and (IV). Any of these processes may be used alone, or two or more of them may be used in combination:

(I) A process of preparing a precursor by mixing water, a polyvalent metal compound, an organic acid having a carboxylic group, and an alkali metal source and/or an ammonia source, and adding to the precursor a phosphoric acid source and/or a carbonic acid source;

(II) A process of preparing a precursor by mixing water, a polyvalent metal compound, a phosphoric acid source and/or a carbonic acid source, and an alkali metal source and/or an ammonia source, and adding to the precursor an organic acid having a carboxylic group;

(III) A process of preparing a precursor by mixing water, a polyvalent metal compound and an organic acid having a carboxylic group, and adding to the precursor a phosphoric acid source and an alkali metal source and/or an ammonia source, and/or a carbonic acid source and an alkali metal source and/or an ammonia source; and (IV) A process of preparing a precursor by mixing water, a polyvalent metal compound, an organic acid having a carboxylic group, and a phosphoric acid source and/or a carbonic acid source, and adding to the precursor an alkali metal source and/or an ammonia source.

Among the aforementioned processes, it is preferable to use the process (I) or (III) in order to obtain a more effective sparingly water-soluble quality improver.

In the precursor preparation process (I), an alkali metal salt and/or an ammonium salt of an organic acid having a carboxylic group may be added instead of an organic acid having a carboxylic group and an alkali metal source and/or an ammonia source. Further, a phosphoric acid source and an alkali metal source and/or an ammonia source, and/or a carbonic acid source and an alkali metal source and/or an ammonia source may be added instead of a phosphoric acid source and/or a carbonic acid source. Similarly, in the precursor preparation process (II), an alkali metal salt and/or an ammonium salt of a phosphoric acid, and/or an alkali metal salt and/or an ammonium salt of carbonic acid may be added instead of a phosphoric acid source and/or a carbonic acid source, and an alkali metal salt and/or an ammonium salt.

With regard to the preparation of the precursor of the present invention, the order of mixing water, a metal compound and an organic acid having a carboxylic group is not particularly limited. Further, with regard to the aforementioned processes (II) and (III), the process of adding a phosphoric acid source and an alkali metal source and/or an ammonia source, and/or a carbonic acid source and an alkali metal source and/or an ammonia source is subdivided into the following processes (a), (b) and (c). Any of these processes may be used alone, or two or more of them may be used in combination:

(a) A process of adding at least one of an alkali metal phosphate, an alkali metal condensed phosphate, an alkali metal carbonate, an ammonium salt of phosphoric acid, an ammonium salt of a condensed phosphoric acid, and an ammonium salt of carbonic acid;

(b) A process of adding at least one selected from phosphoric acid, a condensed phosphoric acid, carbonic acid, and urea, and an alkali metal salt and an ammonium salt thereof simultaneously with an alkali metal source and/or an ammonia source; and (c) A process of adding at least one selected from an alkali metal phosphate, an alkali metal condensed phosphate, an alkali metal carbonate, an ammonium salt of phosphoric acid, an ammonium salt of a condensed phosphoric acid, and an ammonium salt of carbonic acid, thereafter, adding an alkali metal source and/or an ammonia source.

A temperature when mixing each component for producing the sparingly water-soluble quality improver of the present invention is not particularly limited. However, the temperature is preferably in the range of 1 to 70° C., and more preferably 10 to 50° C. for obtaining a more effective sparingly water-soluble quality improver. It is preferred to mix all components and then heat to a temperature in the range of 80 to 230° C., since a greater effect tends to be obtained.

When a liquid temperature at the time of mixing exceeds 70° C., coarse particles are likely to be formed in the liquid, so that it becomes difficult to obtain good dispersibility, and therefore it is not preferable. When the liquid temperature is lower than 1° C., on the other hand, water used as a solvent is likely to be frozen, so that it is difficult to obtain a composition having an excellent effect, and therefore it is not preferable.

The pH value of the sparingly water-soluble quality improver of the present invention is usually in the range of 4 to 11 so as to obtain the quality improving effect without any particular problem. However, the pH is preferably in the range of 4.5 to 10.0, and more preferably 5 to 9, considering the influence on plants and the like.

The sparingly water-soluble quality improver of the present invention may be used as it is in a reaction mixture, or may be used in a ground and/or dispersed form using a grinding machine and/or a dispersing machine. The grinding machine and/or the dispersing machine used in the present invention is not particularly specified, and Dyno-Mill, Sand-mill, Coball-Mill and other wet grinding machines, and an ultrasonic dispersing machine, Nanomizer, Microfluidizer, Ultimizer, a homogenizer and other emulsifying and dispersing machines can be preferably used.

The sparingly water-soluble quality improver of the present invention may be used as it is in the form of liquid, or may be used in the form of a dry powder. The drying of the sparingly water-soluble quality improver may be carried out either by drying the reaction mixture as it is, or by drying it after concentration by a filter press, a rotary filter, a membrane filter, an ultracentrifuge and the like. In order to obtain a dried powder having superior physical properties, the former is preferred to use. When drying the sparingly water-soluble quality improver, a dryer is not particularly specified, but it is preferred to dry in an extremely short period of time from the viewpoint of preventing deterioration of the quality improver. From this viewpoint, therefore, it is preferred to use a spray dryer, a slurry dryer using a ceramic medium in a heated fluid state and other droplet spray-type dryers, and a vacuum dryer.

The sparingly water-soluble quality improver of the present invention is preferred to satisfy the following requirements a) and b), and in order to obtain a better effect, it is preferred to satisfy the requirements c) and d), more preferably the requirements e) and f.

a) $0.01 \leq d50 \leq 1.5$
b) $0 \leq \alpha \leq 10$
c) $0.01 \leq d50 \leq 1.0$
d) $0 \leq \alpha \leq 8$
e) $0.01 \leq d50 < 0.6$
f) $0 \leq \alpha \leq 5$
wherein $\alpha = (d90-d10)/d50$
d50: 50% average particle diameter measured by Nanotrac UPA150
d90: 90% average particle diameter measured by Nanotrac UPA150
d10: 10% average particle diameter measured by Nanotrac UPA150

When 50% average particle diameter of the sparingly water-soluble quality improver measured by Nanotrac UPA150 is larger than 1.5 μm, the product is likely to sediment and precipitate in a spreader. As a result, the effect of the quality improver becomes unstable, and therefore it is not preferable. When d50 is smaller than 0.01 μm, on the other hand, an energy cost required for dispersion markedly increases, and therefore it is not economically preferable. When α is larger than 10, the particle size of the sparingly water-soluble quality improver is uneven, and if used for the purpose of preventing peel puffing in mandarin oranges, for example, a stable effect is hardly obtained, and therefore it is not preferable.

The average diameter in particle size distribution of various minerals contained in the sparingly water-soluble quality improver in the present invention is measured and calculated in the following manner:

Measuring apparatus: Nanotrac UPA150 manufactured by Nikkiso Co., Ltd.

Preparation of samples: the sparingly water-soluble quality improver is added dropwise to be 0.2% as a polyvalent metal ion to the following solvent at 20° C., and samples for measuring particle size distribution are prepared.

Solvent: Distilled water

Preliminary dispersion: Ultrasonic dispersion for 60 seconds by using Ultrasodc Homogenizer (manufactured by Nippon Seiki Co., Ltd.)

Measuring temperature: 20.0° C.±2.5° C.

The timing of applying the sparingly water-soluble quality improver of the present invention to plants varies depending on the type of plants to be treated, the purpose of application, and the agricultural field. When used on fruit trees, for example, the timing of applying the quality improver is generally defined as the period of immediately after flower abscission until harvesting time. Specifically, when used for the purpose of improving the quality and preventing peel puffing of mandarin oranges, it is desirable to spray the quality improver 1 to 6 times every 3 to 6 weeks as a leaf application from July through November. On the other hand, for the purpose of reducing bitter pit in apples, for example, it is desirable to spray the quality improver 1 to 6 times every 3 to 6 weeks from 30 days after full bloom. For the purpose of reducing water core in pears or cherries, for example, it is preferable to spray the quality improver 1 to 6 times every 1 week from around 10 days after full bloom. For the purpose of preventing fruit-cracking in fruit trees or fruit vegetables, it is desirable to spray the quality improver 1 to 6 times every 1 to 6 weeks from the optimal time of each fruit tree. In the case of cherries, for example, it is preferable to spray the quality improver 1 to 6 times every 1 to 6 weeks from around 2 weeks after full bloom.

A concentration of the quality improver of the present invention to be applied varies depending on the type and the crop situation of crop plants to be treated, the purpose of application, and the climate and the weather, and is difficult to determine definitely. Generally, however, the quality improver is applied in the range of 1 ppm to 2 wt %, and preferably in the range of 10 ppm to 0.5 wt % as a polyvalent metal ion. When the concentration of the quality improver is less than 1 ppm, the desired effect is hardly obtained in some cases. When the concentration exceeds 2 wt %, on the other hand, an improvement of the effect is hardly obtained, and therefore it is not advantageous due to cost.

There is no problem if the sparingly water-soluble quality improver of the present invention is used in combination with water soluble mineral salts such as calcium lactate, calcium chloride, calcium nitrate, calcium formate, calcium propionate, calcium itaconate, calcium glutamate, calcium malate-citrate, calcium maleate-citrate, magnesium lactate, magnesium sulfate, magnesium chloride, monomagnesium phosphate, dimagnesium phosphate, sodium ferrous citrate, and ferric ammonium citrate; sparingly water-soluble inorganic minerals such as calcium carbonate, magnesium carbonate, calcium hydroxide, magnesium hydroxide, monocalcium phosphate, dicalcium phosphate, tricalcium phosphate, hydroxyapatite, trimagnesium phosphate, and iron phosphate; silicate; and the like, as long as such salts do not damage the effect of the sparingly water-soluble quality improver of the present invention. For the purpose of a further improvement of the effect, a spreading agent, an emulsifying agent, an adjuvant, a pH adjusting agent, a chelating agent and other additives, generally used in agriculture, may be properly added to the sparingly water-soluble quality improver of the present invention. Agrichemicals such as bactericides and insecticides, and other fertilizers may also be added.

Representative examples of suitable spreading agent and emulsifying agent include nonionic surfactants such as polyoxyethylene alkyl ether, polyoxyethylene alkyl allyl ether, polyoxyethylene alkyl ester, polyethylene sorbitan alkyl ester and sorbitan alkyl ester; anionic surfactants such as alkylbenzene sulfonate, alkyl sulfosuccinate, alkyl sulfate, polyoxyethylene alkyl sulfate and allyl sulfonate; cationic surfactants such as laurylamine, alkyl methyl dihydroxyethyl ammonium salt, stearyltrimethyl ammonium chloride, alkyldimethylbenzyl ammonium chloride and polyoxyethylene alkylamine; ampholytic surfactants such as lauryl betaine, stearyl betaine and imidazolinium betaine. These surfactants may be used alone or, if necessary, two or more of them may be used in combination. Representative examples of suitable adjuvant include polyvinyl alcohol, carboxymethyl cellulose, gum arabic, polyvinyl acetate, gelatine, casein, sodium alginate, propylene glycol alginate ester, xanthan gum, paraffine, tragacanth gum, and the like. They may be used alone or, if necessary, two or more of them may be used in combination.

EXAMPLES

The present invention will be described in more detail below by presenting examples and comparative examples, but it should be noted that the present invention is not limited to these examples.

Example 1

A precursor was prepared by mixing and stirring 666 g of water and 74 g of calcium hydroxide, then adding 112 g of 45% potassium hydroxide, and then adding dropwise 115.2 g of 50% citric acid over a period of about 10 minutes. To the precursor, 196 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and $\alpha=(d90-d10)/d50$ in particle size distribution of the obtained sparingly water-soluble quality improver are shown in Table 1.

Example 2

A precursor was prepared by mixing and stirring 666 g of water and 74 g of calcium hydroxide, and adding dropwise 46.1 g of 50% citric acid over a period of about 10 minutes. To the precursor, a premixed solution of 196 g of 30% phosphoric acid and 44.8 g of 45% potassium hydroxide was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and $\alpha=(d90-d10)/d50$ in particle size distribution of the obtained sparingly water-soluble quality improver are shown in Table 1.

Example 3

A precursor was prepared by mixing and stirring 666 g of water, 74 g of calcium hydroxide, 196 g of 30% phosphoric acid, and 224 g of 45% potassium hydroxide. To the precursor, 230.4 g of 50% citric acid was added and stirred sufficiently. The resulting mixture was then heated at 120° C. for 30 minutes using an autoclave to provide a mixed slurry composition. The slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 4

A precursor was prepared by mixing and stirring 666 g of water, 74 g of calcium hydroxide, 1152 g of 50% citric acid, and 147 g of 40% phosphoric acid. To the precursor, 600 g of 50% sodium hydroxide was added and stirred sufficiently. The resulting mixture was then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 5

A precursor was prepared by mixing and stirring 666 g of water and 74 g of calcium hydroxide, then adding 22.4 g of 45% potassium hydroxide, and then adding dropwise 23.0 g of 50% citric acid over a period of about 5 minutes. To the precursor, 189.5 g of 30% phosphoric acid was added over a period of about 20 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 6

A precursor was prepared by mixing and stirring 666 g of water and 74 g of calcium hydroxide, then adding 61.2 g of 24% aqueous ammonia, and then adding dropwise 115.2 g of 50% citric acid over a period of about 10 minutes. To the precursor, 196 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 7

A precursor was prepared by mixing and stirring 666 g of water and 74 g of calcium hydroxide, then adding 18.6 g of 45% potassium hydroxide, and then adding dropwise 19.2 g of 50% citric acid over a period of about 5 minutes. Into the precursor, 23% carbon dioxide gas was blown at the rate of 4 L/min for 20 minutes, and then at the rate of 0.2 L/min so as to bring the pH to 10. The resulting mixture was heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 8

A precursor was prepared by mixing and stirring 666 g of water and 74 g of calcium hydroxide, then adding dropwise a premixed solution of 25.2 g of 10% potassium hydroxide and 28.8 g of 10% citric acid over a period of about 10 minutes. To the precursor, 179.7 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 9

A precursor was prepared by mixing and stirring 666 g of water and 74 g of calcium hydroxide, then adding 18.7 g of 45% potassium hydroxide, and then adding dropwise 23 g of 50% citric acid over a period of about 10 minutes. To the precursor, 261.3 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 10

A precursor was prepared by mixing and stirring 684 g of water and 56 g of calcium oxide, then adding 9.0 g of 5% potassium hydroxide, and then adding dropwise 26.9 g of 5% citric acid over a period of about 10 minutes. To the precursor, 196 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 11

A precursor was prepared by mixing and stirring 666 g of water and 100 g of calcium carbonate, then adding 112 g of 45% potassium hydroxide, and then adding dropwise 115.2 g of 50% citric acid over a period of about 10 minutes. To the precursor, 39.2 g of 30% phosphoric acid is added over a period of about 20 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 12

A precursor was prepared by mixing and stirring 666 g of water and 74 g of calcium hydroxide, then adding 4604.4 g of 45% potassium hydroxide, and then adding dropwise 4224 g of 50% citric acid over a period of about 60 minutes. To the precursor, 196 g of 30% phosphoric acid is added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 13

A precursor was prepared by mixing and stirring 666 g of water and 74 g of calcium hydroxide, then adding 224 g of 45% potassium hydroxide, and then adding dropwise 230.4 g of 50% citric acid over a period of about 10 minutes. To the precursor, 960 g of 30% phosphoric acid is added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 14

A precursor was prepared by mixing and stirring 666 g of water and 74 g of calcium hydroxide, then adding dropwise a premixed solution of 37.3 g of 45% potassium hydroxide and 7.7 g of 10% citric acid over a period of about 10 minutes. To the precursor, 196 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 15

A precursor was prepared by mixing and stirring 666 g of water and 74 g of calcium hydroxide, then adding 22.4 g of 1% potassium hydroxide, and then adding dropwise 115.2 g of 50% citric acid over a period of about 10 minutes. To the precursor, 196 g of 30% phosphoric acid is added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 16

A precursor was prepared by mixing and stirring 666 g of water and 74 g of calcium hydroxide, and then adding dropwise 230.4 g of 50% citric acid over a period of about 10 minutes. To the precursor, 460.7 g of 30% potassium carbonate was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 17

A precursor was prepared by mixing and stirring 522 g of water and 58 g of magnesium hydroxide, then adding 4.5 g of 45% potassium hydroxide, and then adding dropwise 23.0 g of 10% citric acid over a period of about 10 minutes. To the precursor, 179.7 g of 30% phosphoric acid is added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 18

A precursor was prepared by mixing and stirring 823 g of water, 39.9 g of ferric oxide and 37 g of calcium hydroxide, then adding 2488.9 g of 45% potassium hydroxide, and then adding dropwise 3072 g of 50% citric acid over a period of about 20 minutes. To the precursor, 222.1 g of 30% phosphoric acid was added over a period of about 30 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 19

A precursor was prepared by mixing and stirring 666 g of water and 37 g of calcium hydroxide, then adding 56 g of 45% potassium hydroxide, and then adding dropwise 57.6 g of 50% citric acid over a period of about 10 minutes. To the precursor, 98 g of 30% phosphoric acid was added over a period of about 30 minutes. The resulting mixture was stirred sufficiently, and then heated at 120° C. for 30 minutes using an autoclave to provide a mixed slurry. The mixed slurry was dried by a spray dryer. To the resulting dried product, 86.1 g of commercially available calcium sulfate dihydrate was added to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 20

A precursor was prepared by mixing and stirring 666 g of water and 74 g of calcium hydroxide, and then adding dropwise 192 g of 50% citric acid over a period of about 10 minutes. To the precursor, 345.5 g of 30% potassium carbonate was added over a period of about 30 minutes, and then 49 g of 30% phosphoric acid was added over a period of about 10 minutes. The resulting mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Example 21

A mixture was prepared by mixing and stirring 800 g of water and 200 g of commercially available tricalcium phosphate (manufactured by YONEYAMA Chemical CO., LTD.), and then adding dropwise 192 g of 30% tripotassium citrate over a period of about 10 minutes. The mixture was stirred sufficiently, and then heated at 120° C. for 30 minutes using an autoclave to provide a mixed slurry. The mixed slurry was then dried by a spray dryer to obtain a sparingly water-soluble quality improver.

The molar ratio of each component at the time of reaction as well as d50, d90, d10, and α=(d90−d10)/d50 in particle size distribution of the obtained sparingly water-soluble quality improver are shown in Table 1.

Comparative Example 1

A sparingly water-soluble quality improver was obtained in the same manner as in Example 1 except that an organic acid having a carboxylic group was not added.

The molar ratio of each component at the time of reaction as well as d50, d90, d10, and α=(d90−d10)/d50 in particle size distribution of the obtained sparingly water-soluble quality improver are shown in Table 1.

Comparative Example 2

A sparingly water-soluble quality improver was obtained in the same manner as in Example 1 except that an alkali metal was not added.

The molar ratio of each component at the time of reaction as well as d50, d90, d10, and α=(d90−d10)/d50 in particle size distribution of the obtained sparingly water-soluble quality improver are shown in Table 1.

Comparative Example 3

A preparation having the same composition (containing 75% calcium carbonate, 20% calcium lactate, and 5% PVA) as Preparation Example No. 4 disclosed in Japanese Examined Patent Publication No. S59-19923 was prepared.

The molar ratio of each component at the time of reaction as well as d50, d90, d10, and α=(d90−d10)/d50 in particle size distribution of the obtained sparingly water-soluble quality improver are shown in Table 1.

Comparative Example 4

A commercially available reagent of dicalcium phosphate was group to reduce the particle size to 10 μm or less according to the method of Example 2D disclosed in Japanese Examined Patent Publication No. H2-33349, and used as a preparation.

The molar ratio of each component at the time of reaction as well as d50, d90, d10, and α=(d90−d10)/d50 in particle size distribution of the obtained sparingly water-soluble quality improver are shown in Table 1.

TABLE 1

|  | Polyvalent metal compound A | Organid acid B | Alkali metal compound and/or ammonia source C | Phosphoric acid source and/or carbonic acid source D | A/B molar ratio | A/C molar ratio | A/D molar ratio | D50 | D90 | D10 | α | Process |
|---|---|---|---|---|---|---|---|---|---|---|---|---|
| Ex. 1 | Ca(OH)$_2$ | citric acid | KOH | phosphoric acid | 3.33 | 1.11 | 1.67 | 0.098 | 0.168 | 0.064 | 1.06 | I |
| Ex. 2 | Ca(OH)$_2$ | citric acid | KOH | phosphoric acid | 8.33 | 2.78 | 1.67 | 0.117 | 0.189 | 0.069 | 1.03 | III |
| Ex. 3 | Ca(OH)$_2$ | citric acid | KOH | phosphoric acid | 1.67 | 0.56 | 1.67 | 0.093 | 0.154 | 0.055 | 1.06 | II |
| Ex. 4 | Ca(OH)$_2$ | citric acid | NaOH | phosphoric acid | 0.33 | 0.13 | 1.67 | 0.081 | 0.133 | 0.050 | 1.02 | IV |
| Ex. 5 | Ca(OH)$_2$ | citric acid | KOH | phosphoric acid | 16.67 | 5.56 | 1.72 | 0.119 | 0.177 | 0.082 | 0.80 | I |
| Ex. 6 | Ca(OH)$_2$ | citric acid | ammonia | phosphoric acid | 3.33 | 1.11 | 1.67 | 0.221 | 0.357 | 0.101 | 1.16 | I |
| Ex. 7 | Ca(OH)$_2$ | citric acid | KOH | carbon dioxide gas | 20.00 | 6.67 | 1.00 | 0.131 | 0.221 | 0.093 | 0.98 | I |
| Ex. 8 | Ca(OH)$_2$ | citric acid | KOH | phosphoric acid | 66.67 | 22.22 | 1.82 | 0.149 | 0.263 | 0.093 | 1.14 | I |
| Ex. 9 | Ca(OH)$_2$ | citric acid | KOH | phosphoric acid | 16.67 | 6.67 | 1.25 | 0.403 | 1.672 | 0.178 | 3.71 | I |
| Ex. 10 | CaO | citric acid | KOH | phosphoric acid | 142.86 | 125.00 | 1.67 | 0.630 | 2.468 | 0.174 | 3.64 | I |
| Ex. 11 | CaCO$_3$ | citric acid | KOH | phosphoric acid | 3.33 | 1.11 | 8.33 | 0.295 | 2.254 | 0.180 | 7.03 | I |
| Ex. 12 | Ca(OH)$_2$ | citric acid | KOH | phosphoric acid | 0.09 | 0.027 | 1.67 | 0.073 | 0.110 | 0.050 | 0.82 | I |
| Ex. 13 | Ca(OH)$_2$ | citric acid | KOH | phosphoric acid | 1.67 | 0.56 | 0.67 | 0.359 | 0.507 | 0.231 | 0.77 | I |
| Ex. 14 | Ca(OH)$_2$ | citric acid | KOH | phosphoric acid | 250.00 | 3.33 | 1.67 | 2.914 | 4.170 | 1.822 | 0.81 | I |
| Ex. 15 | Ca(OH)$_2$ | citric acid | KOH | phosphoric acid | 3.33 | 250.00 | 1.67 | 0.523 | 5.826 | 0.017 | 11.11 | I |
| Ex. 16 | Ca(OH)$_2$ | citric acid | —[1] | potassium carbonate | 3.33 | 1.11 | 0.56 | 1.699 | 2.353 | 0.163 | 1.29 | I |
| Ex. 17 | Mg(OH)$_2$ | citric acid | KOH | phosphoric acid | 83.33 | 27.78 | 1.82 | 0.106 | 0.305 | 0.063 | 2.28 | I |

TABLE 1-continued

| | Polyvalent metal compound A | Organic acid B | Alkali metal compound and/or ammonia source C | Phosphoric acid source and/or carbonic acid source D | A/B molar ratio | A/C molar ratio | A/D molar ratio | D50 | D90 | D10 | α | Process |
|---|---|---|---|---|---|---|---|---|---|---|---|---|
| Ex. 18 | Fe$_2$O$_3$ Ca(OH)$_2$ | citric acid | KOH | phosphoric acid | 0.13 | 0.05 | 1.47 | 0.126 | 0.227 | 0.083 | 1.14 | I |
| Ex. 19 | Ca(OH)$_2$ | citric acid | KOH | phosphoric acid | 3.33 | 1.11 | 1.67 | 0.073 | 0.116 | 0.049 | 0.92 | I |
| Ex. 20 | Ca(OH)$_2$ | citric acid | potassium carbonate | potassium carbonate phosphoric acid | 2.00 | 0.67 | 1.11 | 0.080 | 0.122 | 0.049 | 0.91 | I |
| Ex. 21 | Ca$_3$(PO$_4$)$_2$ | potassium citrate | —[2] | —[3] | 20.00 | 6.67 | 1.67 | 0.524 | 3.127 | 0.172 | 5.64 | I |
| Comp. Ex. 1 | Ca(OH)$_2$ | — | KOH | phosphoric acid | — | 1.11 | 1.67 | 3.424 | 4.716 | 2.257 | 0.72 | — |
| Comp. Ex. 2 | Ca(OH)$_2$ | citric acid | — | phosphoric acid | 3.33 | — | 1.67 | 1.985 | 2.385 | 1.636 | 0.38 | — |
| Comp. Ex. 3 | CaCO$_3$ | — | — | — | — | — | — | 0.823 | 3.569 | 0.215 | 4.08 | — |
| Comp. Ex. 4 | CaHPO$_4$ | — | — | — | — | — | — | 0.915 | 4.725 | 0.125 | 5.03 | — |

[1])Potassium carbonate as a carbonic acid source functions as an alkali metal compound.
[2])Potassium citrate as an organic acid functions as an alkali metal compound.
[3])Polyvalent metal compound Ca$_3$(PO$_4$)$_2$ functions as a phosphoric acid source.

Production Process in Table 1:

(I) A precursor is prepared by mixing water, a polyvalent metal compound, an organic acid having a carboxylic group and an alkali metal source. To the precursor, a phosphoric acid source and/or a carbonic acid source are added.

(II) A precursor is prepared by mixing water, a polyvalent metal compound, a phosphoric acid source and/or a carbonic acid source, and an alkali metal source. To the precursor, an organic acid having a carboxylic group is added.

(III) A precursor is prepared by mixing water, a polyvalent metal compound, and an organic acid having a carboxylic group. To the precursor, a phosphoric acid source and an alkali metal source, and/or a carbonic acid source and an alkali metal source are added.

(IV) A precursor is prepared by mixing water, a polyvalent metal compound, an organic acid having a carboxylic group, and a phosphoric acid source and/or a carbonic acid source. To the precursor, an alkali metal source is added.

Application Example 1

The effects of a quality improver in preventing peel puffing and improving fruit quality were evaluated using a mandarin orange tree (Satsuma mandarin). That is, the quality improver of Example 1 was sprayed on the mandarin orange tree at the polyvalent metal concentrations shown in Table 2 over three times from early September (one-month interval). Each treatment was conducted on each branch by spraying with a backpack sprayer.

The evaluation was carried out on 20 randomly selected fruits. The degree of peel puffing was evaluated by examining cross sections of the fruits based on a 4-point scale (none=0, mild=1, moderate=2, severe=3), and expressed by the following equation: peel puffing index={(1×the number of fruits with mild peel puffing)+(2×the number of fruits with moderate peel puffing)+(3×the number of fruits with severe peel puffing)}×100/(3×the number of fruits examined). The fruit skin color was determined using a color chart based on a scale of 0 (poorly colored) to 12 (fully colored). The sugar content was determined using a sugar refractometer. The acidity was expressed as titratable citric acid content. The dirt on a fruit surface was evaluated by a ratio of the surface area soiled whitish to the total surface area of the fruit on a scale of 1 to 5 (not soiled=1, slightly soiled=2, a little soiled=3, moderately soiled=4, much soiled=5). The phytotoxicity was evaluated on a scale of 1 to 5 (normal=1, slightly damaged=2, a little damaged=3, moderately damaged=4, much damaged=5). The results are shown in Table 2.

Application Examples 2 to 21, Comparative Application Examples 1 to 4

The examinations were carried out in the same manner as in Application Example 1 except that the quality improvers of Examples 2 to 21 and Comparative Examples 1 to 4 were used instead of the quality improver of Example 1. The results are shown in Tables 2 and 3.

Comparative Application Example 5

The examination was carried out in the same manner as in Application Example 1 except that calcium formate was used instead of the quality improver of Example 1. The results are shown in Table 3.

Comparative Application Example 6

The examination was carried out in the same manner as in Application Example 1 except that the preparation containing 57% calcium sulfate dihydrate, 27% calcium chloride, and 16% dispersing agent etc. was used instead of the quality improver of Example 1. The results are shown in Table 3.

Comparative Application Example 7

The examination was carried out in the same manner as in Application Example 1 except that calcium chloride was used instead of the quality improver of Example 1. The results are shown in Table 3.

Comparative Application Example 8

The examination was carried out in the same manner as in Application Example 1 except that water (control) was used instead of the quality improver of Example 1. The results are shown in Table 3.

TABLE 2

| | Quality improver used | Polyvalent metal (wt. %) | Degree of peel puffing | Fruit skin color | Sugar content | Acidity | Dirt on a fruit surface | Phytotoxicity |
|---|---|---|---|---|---|---|---|---|
| Appl. Ex. 1 | quality improver of Ex. 1 | 0.030 | 12.5 | 11.0 | 12.8 | 0.85 | 1 | 1 |
| | | 0.075 | 7.5 | 11.8 | 13.3 | 0.86 | 1 | 1 |
| Appl. Ex. 2 | quality improver of Ex. 2 | 0.030 | 18.0 | 11.0 | 12.6 | 0.83 | 1 | 1 |
| | | 0.075 | 11.5 | 11.5 | 13.1 | 0.85 | 1 | 1 |
| Appl. Ex. 3 | quality improver of Ex. 3 | 0.030 | 15.5 | 11.2 | 13.0 | 0.87 | 1 | 1 |
| | | 0.075 | 7.5 | 11.6 | 13.8 | 0.88 | 1 | 1 |
| Appl. Ex. 4 | quality improver of Ex. 4 | 0.030 | 12.5 | 11.3 | 13.1 | 0.88 | 1 | 1 |
| | | 0.075 | 7.5 | 11.6 | 13.8 | 0.89 | 1 | 1 |
| Appl. Ex. 5 | quality improver of Ex. 5 | 0.030 | 20.5 | 11.0 | 12.5 | 0.80 | 1 | 1 |
| | | 0.075 | 18.0 | 11.2 | 12.8 | 0.83 | 1 | 1 |
| Appl. Ex. 6 | quality improver of Ex. 6 | 0.030 | 27.5 | 10.6 | 12.3 | 0.89 | 1 | 1 |
| | | 0.075 | 23.0 | 11.0 | 12.6 | 0.91 | 1 | 1 |
| Appl. Ex. 7 | quality improver of Ex. 7 | 0.030 | 25.0 | 10.2 | 12.0 | 0.92 | 1 | 1 |
| | | 0.075 | 27.5 | 10.5 | 12.3 | 0.90 | 1 | 1 |
| Appl. Ex. 8 | quality improver of Ex. 8 | 0.030 | 35.0 | 10.8 | 11.9 | 0.86 | 1 | 1 |
| | | 0.075 | 30.0 | 11.3 | 12.2 | 0.89 | 2 | 1 |
| Appl. Ex. 9 | quality improver of Ex. 9 | 0.030 | 32.5 | 11.8 | 12.1 | 0.92 | 2 | 1 |
| | | 0.075 | 25.0 | 12.1 | 12.4 | 0.90 | 2 | 1 |
| Appl. Ex. 10 | quality improver of Ex. 10 | 0.030 | 40.0 | 10.0 | 11.6 | 0.92 | 2 | 1 |
| | | 0.075 | 45.0 | 10.5 | 11.9 | 0.94 | 3 | 1 |
| Appl. Ex. 11 | quality improver of Ex. 11 | 0.030 | 37.5 | 10.8 | 12.1 | 0.93 | 2 | 1 |
| | | 0.075 | 32.5 | 11.0 | 12.7 | 0.89 | 3 | 1 |
| Appl. Ex. 12 | quality improver of Ex. 12 | 0.030 | 12.5 | 11.2 | 13.5 | 1.02 | 1 | 2 |
| | | 0.075 | 7.5 | 11.5 | 13.2 | 1.08 | 1 | 2 |
| Appl. Ex. 13 | quality improver of Ex. 13 | 0.030 | 38.5 | 10.9 | 12.6 | 0.91 | 1 | 1 |
| | | 0.075 | 31.5 | 11.1 | 12.8 | 0.94 | 2 | 1 |
| Appl. Ex. 14 | quality improver of Ex. 14 | 0.030 | 42.0 | 11.0 | 11.8 | 0.88 | 3 | 1 |
| | | 0.075 | 40.5 | 11.2 | 12.1 | 0.86 | 3 | 1 |
| Appl. Ex. 15 | quality improver of Ex. 15 | 0.030 | 42.5 | 11.1 | 11.6 | 0.85 | 2 | 1 |
| | | 0.075 | 48.5 | 11.4 | 12.0 | 0.87 | 3 | 1 |
| Appl. Ex. 16 | quality improver of Ex. 16 | 0.030 | 32.0 | 10.5 | 12.5 | 0.92 | 2 | 2 |
| | | 0.075 | 28.0 | 10.9 | 12.9 | 0.95 | 3 | 2 |
| Appl. Ex. 17 | quality improver of Ex. 17 | 0.030 | 42.5 | 10.9 | 12.3 | 0.98 | 1 | 1 |
| | | 0.075 | 35.0 | 10.4 | 12.8 | 0.99 | 2 | 1 |
| Appl. Ex. 18 | quality improver of Ex. 18 | 0.030 | 30.0 | 11.0 | 12.8 | 0.98 | 1 | 2 |
| | | 0.075 | 27.5 | 11.2 | 12.0 | 1.05 | 1 | 2 |
| Appl. Ex. 19 | quality improver of Ex. 19 | 0.030 | 20.5 | 10.8 | 12.1 | 0.88 | 1 | 1 |
| | | 0.075 | 18.0 | 10.9 | 12.3 | 0.86 | 1 | 1 |
| Appl. Ex. 20 | quality improver of Ex. 20 | 0.030 | 27.5 | 10.0 | 12.9 | 0.90 | 1 | 1 |
| | | 0.075 | 22.5 | 10.8 | 13.1 | 0.93 | 1 | 1 |
| Appl. Ex. 21 | quality improver of Ex. 21 | 0.030 | 52.5 | 9.5 | 11.0 | 0.99 | 2 | 1 |
| | | 0.075 | 47.5 | 9.8 | 11.4 | 0.98 | 3 | 1 |

TABLE 3

| | Quality improver used | Polyvalent metal (wt. %) | Degree of peel puffing | Fruit skin color | Sugar content | Acidity | Dirt on a fruit surface | Phytotoxicity |
|---|---|---|---|---|---|---|---|---|
| Comp. Appl. Ex. 1 | quality improver of Comp. Ex. 1 | 0.030 | 60.0 | 10.0 | 10.1 | 0.93 | 4 | 1 |
| | | 0.075 | 57.5 | 10.2 | 10.8 | 0.97 | 5 | 1 |
| Comp. Appl. Ex. 2 | quality improver of Comp. Ex. 2 | 0.030 | 62.5 | 10.6 | 11.5 | 0.93 | 3 | 1 |
| | | 0.075 | 57.5 | 10.8 | 11.8 | 0.95 | 4 | 1 |
| Comp. Appl. Ex. 3 | quality improver of Comp. Ex. 3 | 0.030 | 56.5 | 9.5 | 9.8 | 0.97 | 3 | 1 |
| | | 0.075 | 49.5 | 9.8 | 10.0 | 0.99 | 3 | 1 |
| Comp. Appl. Ex. 4 | quality improver of Comp. Ex. 4 | 0.030 | 60.0 | 10.7 | 9.9 | 0.98 | 3 | 1 |
| | | 0.075 | 52.5 | 10.9 | 10.3 | 0.99 | 4 | 1 |
| Comp. Appl. Ex. 5 | calcium formate | 0.030 | 47.5 | 10.0 | 10.5 | 0.93 | 1 | 3 |
| | | 0.075 | 42.5 | 10.4 | 11.1 | 0.95 | 1 | 3 |
| Comp. Appl. Ex. 6 | preparation: $CaSO_4 \cdot 2H_2O$ 57%, $CaCl_2$ 27%, dispersing agent 16% | 0.030 | 45.0 | 10.1 | 10.2 | 0.94 | 1 | 2 |
| | | 0.075 | 40.0 | 10.5 | 10.5 | 0.97 | 1 | 2 |
| Comp. Appl. Ex. 7 | calcium chloride | 0.030 | 47.0 | 9.5 | 10.0 | 1.00 | 1 | 4 |
| | | 0.075 | 42.0 | 9.9 | 10.1 | 0.99 | 1 | 4 |
| Comp. Appl. Ex. 8 | water (control) | — | 80.0 | 8.6 | 9.6 | 1.05 | 1 | 1 |

Application Example 22

The effects of a quality improver in reducing bitter pit and improving fruit quality were evaluated using an apple tree (Orin). That is, the quality improver of Example 1 was sprayed on the apple tree at the polyvalent metal concentrations shown in Table 4 over four times from early June (two-week interval). Each treatment was conducted on each branch by spraying with a backpack sprayer.

The evaluation was carried out on 50 randomly selected fruits. The incidence of bitter pit was expressed as a ratio of the number of fruits with bitter pit to the total number of fruits examined. The ground color of fruit skin was determined on a 5-point scale (best=5, worst=1). The sugar content was determined using a sugar refractometer. The acidity was expressed as titratable malic acid content. The phytotoxicity was evaluated on a scale of 1 to 5 (normal=1, slightly damaged=2, a little damaged=3, moderately damaged=4, much damaged=5). The results are shown in Table 4.

Application Examples 23 to 42, Comparative Application Examples 9 to 12

The examinations were carried out in the same manner as in Application Example 22 except that the quality improvers of Examples 2 to 21 and Comparative Examples 1 to 4 were used instead of the quality improver of Example 1. The results are shown in Tables 4 and 5.

Comparative Application Example 13

The examination was carried out in the same manner as in Application Example 22 except that calcium formate was used instead of the quality improver of Example 1. The results are shown in Table 5.

Comparative Application Example 14

The examination was carried out in the same manner as in Application Example 22 except that the preparation containing 57% calcium sulfate dihydrate, 27% calcium chloride, and 16% dispersing agent etc. was used instead of the quality improver of Example 1. The results are shown in Table 5.

Comparative Application Example 15

The examination was carried out in the same manner as in Application Example 22 except that calcium chloride was used instead of the quality improver of Example 1. The results are shown in Table 5.

Comparative Application Example 16

The examination was carried out in the same manner as in Application Example 22 except that water (control) was used instead of the quality improver of Example 1. The results are shown in Table 5.

TABLE 4

| | Quality improver used | Polyvalent metal (wt. %) | Incidence of bitter pit (%) | Ground color | Sugar content | Acidity | Phytotoxicity |
|---|---|---|---|---|---|---|---|
| Appl. Ex. 22 | quality improver of Ex. 1 | 0.030 | 6.0 | 4.5 | 16.1 | 0.30 | 1 |
| | | 0.075 | 4.0 | 4.7 | 16.3 | 0.31 | 1 |
| Appl. Ex. 23 | quality improver of Ex. 2 | 0.030 | 4.0 | 4.6 | 16.5 | 0.28 | 1 |
| | | 0.075 | 4.0 | 4.7 | 16.7 | 0.30 | 1 |
| Appl. Ex. 24 | quality improver of Ex. 3 | 0.030 | 4.0 | 4.7 | 16.0 | 0.32 | 1 |
| | | 0.075 | 4.0 | 4.6 | 16.8 | 0.33 | 1 |
| Appl. Ex. 25 | quality improver of Ex. 4 | 0.030 | 6.0 | 4.3 | 16.2 | 0.33 | 1 |
| | | 0.075 | 4.0 | 4.2 | 16.8 | 0.34 | 1 |
| Appl. Ex. 26 | quality improver of Ex. 5 | 0.030 | 8.0 | 4.2 | 16.0 | 0.25 | 1 |
| | | 0.075 | 6.0 | 4.1 | 16.4 | 0.27 | 1 |
| Appl. Ex. 27 | quality improver of Ex. 6 | 0.030 | 8.0 | 4.1 | 15.8 | 0.29 | 1 |
| | | 0.075 | 8.0 | 4.0 | 15.9 | 0.31 | 1 |
| Appl. Ex. 28 | quality improver of Ex. 7 | 0.030 | 10.0 | 4.0 | 15.3 | 0.32 | 1 |
| | | 0.075 | 8.0 | 4.2 | 15.5 | 0.30 | 1 |
| Appl. Ex. 29 | quality improver of Ex. 8 | 0.030 | 10.0 | 4.2 | 15.4 | 0.26 | 1 |
| | | 0.075 | 10.0 | 4.3 | 15.7 | 0.29 | 1 |
| Appl. Ex. 30 | quality improver of Ex. 9 | 0.030 | 10.0 | 4.3 | 15.1 | 0.32 | 1 |
| | | 0.075 | 10.0 | 4.4 | 15.3 | 0.30 | 1 |
| Appl. Ex. 31 | quality improver of Ex. 10 | 0.030 | 18.0 | 3.8 | 15.0 | 0.32 | 1 |
| | | 0.075 | 16.0 | 3.9 | 15.2 | 0.34 | 1 |
| Appl. Ex. 32 | quality improver of Ex. 11 | 0.030 | 16.0 | 4.0 | 15.1 | 0.33 | 1 |
| | | 0.075 | 16.0 | 4.1 | 15.2 | 0.29 | 1 |
| Appl. Ex. 33 | quality improver of Ex. 12 | 0.030 | 12.0 | 4.2 | 16.5 | 0.39 | 2 |
| | | 0.075 | 8.0 | 4.4 | 16.2 | 0.38 | 2 |
| Appl. Ex. 34 | quality improver of Ex. 13 | 0.030 | 20.0 | 4.0 | 15.4 | 0.31 | 1 |
| | | 0.075 | 18.0 | 4.1 | 15.8 | 0.34 | 1 |
| Appl. Ex. 35 | quality improver of Ex. 14 | 0.030 | 22.0 | 3.9 | 14.8 | 0.30 | 1 |
| | | 0.075 | 18.0 | 4.0 | 15.1 | 0.32 | 1 |
| Appl. Ex. 36 | quality improver of Ex. 15 | 0.030 | 16.0 | 4.0 | 14.7 | 0.25 | 1 |
| | | 0.075 | 12.0 | 4.0 | 15.0 | 0.27 | 1 |
| Appl. Ex. 37 | quality improver of Ex. 16 | 0.030 | 14.0 | 4.0 | 15.5 | 0.32 | 1 |
| | | 0.075 | 12.0 | 4.1 | 15.7 | 0.35 | 1 |
| Appl. Ex. 38 | quality improver of Ex. 17 | 0.030 | 16.0 | 4.3 | 15.4 | 0.38 | 1 |
| | | 0.075 | 14.0 | 4.3 | 15.6 | 0.39 | 1 |
| Appl. Ex. 39 | quality improver of Ex. 18 | 0.030 | 16.0 | 4.2 | 15.8 | 0.38 | 2 |
| | | 0.075 | 12.0 | 4.3 | 16.2 | 0.39 | 2 |
| Appl. Ex. 40 | quality improver of Ex. 19 | 0.030 | 12.0 | 4.2 | 15.8 | 0.35 | 1 |
| | | 0.075 | 10.0 | 4.3 | 16.0 | 0.34 | 1 |
| Appl. Ex. 41 | quality improver of Ex. 20 | 0.030 | 14.0 | 4.3 | 15.9 | 0.30 | 1 |
| | | 0.075 | 10.0 | 4.3 | 16.0 | 0.33 | 1 |

TABLE 4-continued

| | Quality improver used | Polyvalent metal (wt. %) | Incidence of bitter pit (%) | Ground color | Sugar content | Acidity | Phytotoxicity |
|---|---|---|---|---|---|---|---|
| Appl. Ex. 42 | quality improver of Ex. 21 | 0.030 | 28.0 | 3.5 | 14.9 | 0.39 | 1 |
| | | 0.075 | 26.0 | 3.7 | 14.9 | 0.38 | 1 |

TABLE 5

| | Quality improver used | Polyvalent metal (wt. %) | Incidence of bitter pit (%) | Ground color | Sugar content | Acidity | Phytotoxicity |
|---|---|---|---|---|---|---|---|
| Comp. Appl. Ex. 9 | quality improver of Comp. Ex. 1 | 0.030 | 35.0 | 3.8 | 14.2 | 0.38 | 1 |
| | | 0.075 | 32.0 | 3.9 | 14.4 | 0.38 | 1 |
| Comp. Appl. Ex. 10 | quality improver of Comp. Ex. 2 | 0.030 | 34.0 | 3.7 | 14.5 | 0.34 | 1 |
| | | 0.075 | 30.0 | 3.8 | 14.8 | 0.35 | 1 |
| Comp. Appl. Ex. 11 | quality improver of Comp. Ex. 3 | 0.030 | 30.0 | 3.7 | 13.8 | 0.40 | 1 |
| | | 0.075 | 32.0 | 3.6 | 14.0 | 0.41 | 1 |
| Comp. Appl. Ex. 12 | quality improver of Comp. Ex. 4 | 0.030 | 36.0 | 3.8 | 13.9 | 0.33 | 1 |
| | | 0.075 | 30.0 | 3.9 | 14.3 | 0.34 | 1 |
| Comp. Appl. Ex. 13 | calcium formate | 0.030 | 26.0 | 3.8 | 14.5 | 0.38 | 3 |
| | | 0.075 | 24.0 | 3.8 | 14.9 | 0.30 | 3 |
| Comp. Appl. Ex. 14 | preparation: $CaSO_4 \cdot 2H_2O$ 57%, $CaCl_2$ 27%, dispersing agent 16% | 0.030 | 28.0 | 3.9 | 14.2 | 0.39 | 2 |
| | | 0.075 | 26.0 | 3.9 | 14.5 | 0.32 | 2 |
| Comp. Appl. Ex. 15 | calcium chloride | 0.030 | 30.0 | 3.7 | 14.1 | 0.37 | 4 |
| | | 0.075 | 25.0 | 3.9 | 14.2 | 0.35 | 4 |
| Comp. Appl. Ex. 16 | water (control) | — | 41.0 | 3.5 | 13.6 | 0.42 | 1 |

Application Example 43

The effects of a quality improver in reducing leaf blight and improving fruit quality were evaluated using a Welsh onion plant (Sakaiyakko).

That is, the quality improver of Example 1 was sprayed on the Welsh onion at the polyvalent metal concentrations shown in Table 7 over three times from early June (one-week interval) using a backpack sprayer.

The evaluation was carried out on 50 randomly selected plants. The leaf blight was determined by evaluating the degree of leaf blight based on a 4-point scale (none=0, mild=1, moderate=2, severe=3), and expressed by the following equation: leaf blight index={(1×the number of plants with mild leaf blight)+(2×the number of plants with moderate leaf blight)+(3×the number of plants with severe leaf blight)}×100/(3× the number of plants examined). In addition, plant length, plant weight, the number of leaves, and yield were evaluated. The dirt on a leaf surface was evaluated by a ratio of the surface area soiled whitish to the total surface area of the leaf on a scale of 1 to 5 (not soiled=1, slightly soiled=2, a little soiled=3, moderately soiled=4, much soiled=5). The phytotoxicity was evaluated on a scale of 1 to 5 (normal=1, slightly damaged=2, a little damaged=3, moderately damaged=4, much damaged=5). The results are shown in Table 6.

Application Examples 44 to 63, Comparative Application Examples 17 to 20

The examinations were carried out in the same manner as in Application Example 43 except that the quality improvers of Examples 2 to 21 and Comparative Examples 1 to 4 were used instead of the quality improver of Example 1. The results are shown in Tables 6 and 7.

Comparative Application Example 21

The examination was carried out in the same manner as in Application Example 43 except that calcium formate was used instead of the quality improver of Example 1. The results are shown in Table 7.

Comparative Application Example 22

The examination was carried out in the same manner as in Application Example 43 except that the preparation containing 57% calcium sulfate dihydrate, 27% calcium chloride, and 16% dispersing agent etc. was used instead of the quality improver of Example 1. The results are shown in Table 7.

Comparative Application Example 23

The examination was carried out in the same manner as in Application Example 43 except that calcium chloride was used instead of the quality improver of Example 1. The results are shown in Table 7.

Comparative Application Example 24

The examination was carried out in the same manner as in Application Example 43 except that water (control) was used instead of the quality improver of Example 1. The results are shown in Table 7.

TABLE 6

| | Quality improver used | Polyvalent metal (wt. %) | Leaf blight | Plant length (cm) | Plant weight (g) | Number of leaves | Dirt on a leaf surface | Phytotoxicity |
|---|---|---|---|---|---|---|---|---|
| Appl. Ex. 43 | quality improver of Ex. 1 | 0.030 | 12.0 | 68.3 | 221 | 40.2 | 1 | 1 |
| | | 0.075 | 8.0 | 68.5 | 234 | 41.3 | 1 | 1 |
| Appl. Ex. 44 | quality improver of Ex. 2 | 0.030 | 16.5 | 69.4 | 243 | 38.5 | 1 | 1 |
| | | 0.075 | 13.0 | 70.3 | 245 | 40.2 | 1 | 1 |
| Appl. Ex. 45 | quality improver of Ex. 3 | 0.030 | 18.0 | 67.5 | 230 | 42.1 | 1 | 1 |
| | | 0.075 | 12.0 | 69.2 | 238 | 41.5 | 1 | 1 |
| Appl. Ex. 46 | quality improver of Ex. 4 | 0.030 | 13.5 | 67.5 | 232 | 39.4 | 1 | 1 |
| | | 0.075 | 8.0 | 68.9 | 228 | 38.5 | 1 | 1 |
| Appl. Ex. 47 | quality improver of Ex. 5 | 0.030 | 18.0 | 65.3 | 221 | 40.2 | 1 | 1 |
| | | 0.075 | 18.0 | 66.8 | 224 | 40.8 | 1 | 1 |
| Appl. Ex. 48 | quality improver of Ex. 6 | 0.030 | 22.5 | 68.2 | 208 | 38.1 | 1 | 1 |
| | | 0.075 | 18.5 | 65.9 | 219 | 38.9 | 1 | 1 |
| Appl. Ex. 49 | quality improver of Ex. 7 | 0.030 | 25.0 | 64.5 | 223 | 39.4 | 1 | 1 |
| | | 0.075 | 27.5 | 66.9 | 215 | 38.0 | 1 | 1 |
| Appl. Ex. 50 | quality improver of Ex. 8 | 0.030 | 25.0 | 64.3 | 215 | 38.2 | 1 | 1 |
| | | 0.075 | 22.0 | 65.5 | 207 | 37.5 | 2 | 1 |
| Appl. Ex. 51 | quality improver of Ex. 9 | 0.030 | 22.5 | 62.9 | 201 | 37.1 | 2 | 1 |
| | | 0.075 | 20.0 | 63.1 | 203 | 36.6 | 2 | 1 |
| Appl. Ex. 52 | quality improver of Ex. 10 | 0.030 | 30.0 | 58.0 | 206 | 37.0 | 2 | 1 |
| | | 0.075 | 28.0 | 61.8 | 229 | 38.1 | 3 | 1 |
| Appl. Ex. 53 | quality improver of Ex. 11 | 0.030 | 32.5 | 60.2 | 201 | 37.9 | 2 | 1 |
| | | 0.075 | 32.0 | 61.4 | 207 | 35.3 | 3 | 1 |
| Appl. Ex. 54 | quality improver of Ex. 12 | 0.030 | 32.0 | 70.2 | 245 | 40.5 | 1 | 3 |
| | | 0.075 | 28.5 | 71.5 | 252 | 40.8 | 1 | 3 |
| Appl. Ex. 55 | quality improver of Ex. 13 | 0.030 | 26.5 | 62.9 | 224 | 38.9 | 1 | 1 |
| | | 0.075 | 20.5 | 64.1 | 238 | 39.1 | 2 | 1 |
| Appl. Ex. 56 | quality improver of Ex. 14 | 0.030 | 32.0 | 63.9 | 218 | 37.0 | 3 | 1 |
| | | 0.075 | 28.5 | 64.1 | 221 | 38.2 | 3 | 1 |
| Appl. Ex. 57 | quality improver of Ex. 15 | 0.030 | 27.5 | 64.2 | 217 | 38.5 | 2 | 1 |
| | | 0.075 | 23.5 | 64.0 | 230 | 39.1 | 3 | 1 |
| Appl. Ex. 58 | quality improver of Ex. 16 | 0.030 | 25.0 | 61.5 | 211 | 37.0 | 2 | 1 |
| | | 0.075 | 18.0 | 62.9 | 217 | 38.2 | 3 | 1 |
| Appl. Ex. 59 | quality improver of Ex. 17 | 0.030 | 30.5 | 63.2 | 204 | 37.9 | 1 | 1 |
| | | 0.075 | 25.0 | 64.0 | 226 | 39.1 | 2 | 1 |
| Appl. Ex. 60 | quality improver of Ex. 18 | 0.030 | 30.0 | 67.1 | 248 | 40.4 | 1 | 2 |
| | | 0.075 | 28.5 | 65.2 | 239 | 39.5 | 1 | 2 |
| Appl. Ex. 61 | quality improver of Ex. 19 | 0.030 | 19.5 | 66.2 | 231 | 39.3 | 1 | 1 |
| | | 0.075 | 18.0 | 67.4 | 241 | 41.2 | 1 | 1 |
| Appl. Ex. 62 | quality improver of Ex. 20 | 0.030 | 24.5 | 62.8 | 218 | 38.1 | 1 | 1 |
| | | 0.075 | 20.5 | 64.2 | 224 | 37.9 | 1 | 1 |
| Appl. Ex. 63 | quality improver of Ex. 21 | 0.030 | 39.5 | 58.1 | 194 | 34.2 | 2 | 1 |
| | | 0.075 | 36.0 | 60.1 | 199 | 35.1 | 3 | 1 |

TABLE 7

| | Quality improver used | | Polyvalent metal (wt. %) | Leaf blight | Plant length | Plant weight | Number of leaves | Dirt on a leaf surface | Phytotoxicity |
|---|---|---|---|---|---|---|---|---|---|
| Comp. Appl. Ex. 17 | quality improver of Comp. Ex. 1 | | 0.030 | 42.0 | 58.8 | 175 | 30.4 | 4 | 1 |
| | | | 0.075 | 38.0 | 59.9 | 181 | 31.1 | 5 | 1 |
| Comp. Appl. Ex. 18 | quality improver of Comp. Ex. 2 | | 0.030 | 44.0 | 59.7 | 185 | 31.2 | 3 | 1 |
| | | | 0.075 | 35.0 | 60.2 | 188 | 32.3 | 4 | 1 |
| Comp. Appl. Ex. 19 | quality improver of Comp. Ex. 3 | | 0.030 | 34.0 | 58.7 | 168 | 29.8 | 3 | 1 |
| | | | 0.075 | 38.0 | 56.6 | 170 | 30.2 | 3 | 1 |
| Comp. Appl. Ex. 20 | quality improver of Comp. Ex. 4 | | 0.030 | 39.0 | 56.8 | 159 | 32.5 | 3 | 1 |
| | | | 0.075 | 34.0 | 60.9 | 163 | 33.1 | 4 | 1 |
| Comp. Appl. Ex. 21 | calcium formate | | 0.030 | 30.0 | 60.8 | 185 | 34.2 | 1 | 3 |
| | | | 0.075 | 28.0 | 62.8 | 191 | 35.6 | 1 | 3 |
| Comp. Appl. Ex. 22 | preparation: CaSO$_4$•2H$_2$O 57%, CaCl$_2$ 27%, dispersing agent 16% | | 0.030 | 29.0 | 61.9 | 192 | 33.3 | 1 | 2 |
| | | | 0.075 | 25.0 | 62.9 | 195 | 36.1 | 1 | 2 |
| Comp. Appl. Ex. 23 | calcium chloride | | 0.030 | 42.0 | 59.2 | 185 | 30.3 | 1 | 4 |
| | | | 0.075 | 40.0 | 60.9 | 189 | 31.3 | 1 | 4 |
| Comp. Appl. Ex. 24 | water (control) | | — | 48.0 | 56.5 | 156 | 28.0 | 1 | 1 |

Application Example 64

The effects of a quality improver in reducing fruit-cracking and improving fruit quality were evaluated using a grape tree (Pione). That is, the quality improver of Example 1 was sprayed on the grape tree at the polyvalent metal concentrations shown in Table 8 over four times from early July (two-week interval). Each treatment was conducted on each branch by spraying with a backpack sprayer.

The evaluation was carried out on 20 randomly selected clusters. The number of fruit-cracking was expressed as the number of grains with cracking in a cluster examined. The degree of fruit coloring was expressed using a color chart based on a scale of 0 (poorly colored) to 12 (fully colored). The sugar content was determined using a sugar refractometer. The acidity was expressed as titratable tartaric acid content. The dirt on a fruit surface was evaluated by a ratio of the surface area soiled whitish to the total surface area of the fruit on a scale of 1 to 5 (not soiled=1, slightly soiled=2, a little soiled=3, moderately soiled=4, much soiled=5). The phytotoxicity was evaluated on a scale of 1 to 5 (normal=1, slightly damaged=2, a little damaged=3, moderately damaged=4, much damaged=5). The results are shown in Table 8.

Application Examples 65 to 73, Comparative Application Examples 25 to 28

The examinations were carried out in the same manner as in Application Example 64 except that the quality improvers of Examples 2 to 4, 6 to 7, 12, 14, 17 to 18, and Comparative Examples 1 to 4 were used instead of the quality improver of Example 1. The results are shown in Tables 8 and 9.

Comparative Application Example 29

The examination was carried out in the same manner as in Application Example 64 except that calcium formate was used instead of the quality improver of Example 1. The results are shown in Table 9.

Comparative Application Example 30

The examination was carried out in the same manner as in Application Example 64 except that the preparation containing 57% calcium sulfate dihydrate, 27% calcium chloride, and 16% dispersing agent etc. was used instead of the quality improver of Example 1. The results are shown in Table 9.

Comparative Application Example 31

The examination was carried out in the same manner as in Application Example 64 except that calcium chloride was used instead of the quality improver of Example 1. The results are shown in Table 9.

Comparative Application Example 32

The examination was carried out in the same manner as in Application Example 64 except that water (control) was used instead of the quality improver of Example 1. The results are shown in Table 9.

TABLE 8

| | Quality improver used | Polyvalent metal (wt. %) | Number of fruit-cracking | Degree of fruit coloring | Sugar content | Acidity | Dirt on a fruit surface | Phytotoxicity |
|---|---|---|---|---|---|---|---|---|
| Appl. Ex. 64 | quality improver of Ex. 1 | 0.030 | 0.2 | 10.4 | 19.9 | 0.49 | 1 | 1 |
| | | 0.075 | 0.0 | 10.5 | 20.2 | 0.50 | 1 | 1 |
| Appl. Ex. 65 | quality improver of Ex. 2 | 0.030 | 0.4 | 10.3 | 19.8 | 0.48 | 1 | 1 |
| | | 0.075 | 0.3 | 10.2 | 20.2 | 0.48 | 1 | 1 |
| Appl. Ex. 66 | quality improver of Ex. 3 | 0.030 | 0.2 | 10.4 | 20.1 | 0.50 | 1 | 1 |
| | | 0.075 | 0.1 | 10.5 | 20.4 | 0.51 | 1 | 1 |
| Appl. Ex. 67 | quality improver of Ex. 4 | 0.030 | 0.1 | 10.5 | 20.3 | 0.51 | 1 | 1 |
| | | 0.075 | 0.1 | 10.8 | 20.4 | 0.54 | 1 | 1 |
| Appl. Ex. 68 | quality improver of Ex. 6 | 0.030 | 0.5 | 10.2 | 19.5 | 0.48 | 1 | 1 |
| | | 0.075 | 0.3 | 10.4 | 19.9 | 0.49 | 1 | 1 |
| Appl. Ex. 69 | quality improver of Ex. 7 | 0.030 | 0.7 | 10.1 | 19.4 | 0.51 | 1 | 1 |
| | | 0.075 | 0.4 | 10.2 | 19.7 | 0.52 | 1 | 1 |
| Appl. Ex. 70 | quality improver of Ex. 12 | 0.030 | 0.2 | 10.4 | 20.5 | 0.55 | 1 | 2 |
| | | 0.075 | 0.1 | 10.8 | 20.7 | 0.57 | 1 | 2 |
| Appl. Ex. 71 | quality improver of Ex. 14 | 0.030 | 0.6 | 10.2 | 19.4 | 0.48 | 2 | 1 |
| | | 0.075 | 0.4 | 10.4 | 19.6 | 0.48 | 3 | 1 |
| Appl. Ex. 72 | quality improver of Ex. 17 | 0.030 | 0.6 | 10.0 | 19.5 | 0.53 | 1 | 1 |
| | | 0.075 | 0.3 | 10.1 | 19.8 | 0.55 | 2 | 1 |
| Appl. Ex. 73 | quality improver of Ex. 18 | 0.030 | 0.7 | 9.9 | 19.6 | 0.55 | 1 | 2 |
| | | 0.075 | 0.5 | 10.2 | 19.8 | 0.56 | 1 | 2 |

TABLE 9

| | Quality improver used | Polyvalent metal (wt. %) | Number of fruit-cracking | Degree of fruit coloring | Sugar content | Acidity | Dirt on a fruit surface | Phytotoxicity |
|---|---|---|---|---|---|---|---|---|
| Comp. Appl. Ex. 25 | quality improver of Comp. Ex. 1 | 0.030 | 2.9 | 9.7 | 18.9 | 0.53 | 4 | 1 |
| | | 0.075 | 2.6 | 9.2 | 19.1 | 0.55 | 5 | 1 |
| Comp. Appl. Ex. 26 | quality improver of Comp. Ex. 2 | 0.030 | 2.9 | 9.3 | 19.2 | 0.63 | 3 | 1 |
| | | 0.075 | 3.1 | 9.1 | 19.4 | 0.69 | 4 | 1 |
| Comp. Appl. Ex. 27 | quality improver of Comp. Ex. 3 | 0.030 | 2.9 | 9.5 | 18.8 | 0.55 | 3 | 1 |
| | | 0.075 | 2.5 | 9.7 | 18.8 | 0.56 | 3 | 1 |
| Comp. Appl. Ex. 28 | quality improver of Comp. Ex. 4 | 0.030 | 3.0 | 9.3 | 18.6 | 0.58 | 3 | 1 |
| | | 0.075 | 2.9 | 9.6 | 18.9 | 0.57 | 4 | 1 |
| Comp. Appl. Ex. 29 | calcium formate | 0.030 | 3.9 | 9.7 | 18.9 | 0.54 | 1 | 3 |
| | | 0.075 | 3.6 | 9.7 | 19.3 | 0.53 | 1 | 3 |

TABLE 9-continued

| | Quality improver used | Polyvalent metal (wt. %) | Number of fruit-cracking | Degree of fruit coloring | Sugar content | Acidity | Dirt on a fruit surface | Phytotoxicity |
|---|---|---|---|---|---|---|---|---|
| Comp. Appl. Ex. 30 | preparation: CaSO$_4$•2H$_2$O 57%, CaCl$_2$ 27%, dispersing agent 16% | 0.030 | 4.1 | 9.6 | 18.8 | 0.51 | 1 | 2 |
| | | 0.075 | 3.9 | 9.4 | 19.1 | 0.59 | 1 | 2 |
| Comp. Appl. Ex. 31 | calcium chloride | 0.030 | 4.4 | 9.2 | 18.4 | 0.63 | 1 | 4 |
| | | 0.075 | 4.5 | 9.0 | 18.6 | 0.66 | 1 | 4 |
| Comp. Appl. Ex. 32 | water (control) | — | 5.0 | 9.0 | 18.1 | 0.68 | 1 | 1 |

Application Example 74

The effects of a quality improver in reducing fruit-cracking and improving fruit quality were evaluated using a cherry fruit tree (Satonishiki). That is, the quality improver of Example 1 was sprayed on the cherry fruit tree at the polyvalent metal concentrations shown in Table 10 over three times from early May (two-week interval). Each treatment was conducted on each branch by spraying with a backpack sprayer.

The evaluation was carried out on 50 randomly selected fruits. The incidence of fruit-cracking was expressed as a ratio of the number of fruits with cracking to the total number of fruits examined. The degree of fruit coloring was expressed as the colored area of a fruit. The sugar content was determined using a sugar refractometer. The acidity was expressed as titratable malic acid content. The dirt on a fruit surface was evaluated by a ratio of the surface area soiled whitish to the total surface area of the fruit on a scale of 1 to 5 (not soiled=1, slightly soiled=2, a little soiled=3, moderately soiled=4, much soiled=5). The phytotoxicity was evaluated on a scale of 1 to 5 (normal=1, slightly damaged=2, a little damaged=3, moderately damaged=4, much damaged=5). The results are shown in Table 10.

Application Examples 75 to 83, Comparative Application Examples 33 to 36

The examinations were carried out in the same manner as in Application Example 64 except that the quality improvers of Examples 2 to 4, 6 to 7, 12, 14, 17 to 18, and Comparative Examples 1 to 4 were used instead of the quality improver of Example 1. The results are shown in Tables 10 and 11.

Comparative Application Example 37

The examination was carried out in the same manner as in Application Example 74 except that calcium formate was used instead of the quality improver of Example 1. The results are shown in Table 11.

Comparative Application Example 38

The examination was carried out in the same manner as in Application Example 74 except that the preparation containing 57% calcium sulfate dihydrate, 27% calcium chloride, and 16% dispersing agent etc. was used instead of the quality improver of Example 1. The results are shown in Table 11.

Comparative Application Example 39

The examination was carried out in the same manner as in Application Example 74 except that calcium chloride was used instead of the quality improver of Example 1. The results are shown in Table 11.

Comparative Application Example 40

The examination was carried out in the same manner as in Application Example 74 except that water (control) was used instead of the quality improver of Example 1. The results are shown in Table 11.

TABLE 10

| | Quality improver used | Polyvalent metal (wt. %) | Incidence of fruit-cracking (%) | Degree of fruit coloring | Sugar content | Acidity | Dirt on a fruit surface | Phytotoxicity |
|---|---|---|---|---|---|---|---|---|
| Appl. Ex. 74 | quality improver of Ex. 1 | 0.030 | 1.6 | 82.7 | 22.4 | 0.45 | 1 | 1 |
| | | 0.075 | 1.1 | 82.9 | 22.8 | 0.47 | 1 | 1 |
| Appl. Ex. 75 | quality improver of Ex. 2 | 0.030 | 1.7 | 82.2 | 22.2 | 0.44 | 1 | 1 |
| | | 0.075 | 1.4 | 82.4 | 22.5 | 0.46 | 1 | 1 |
| Appl. Ex. 76 | quality improver of Ex. 3 | 0.030 | 1.5 | 82.5 | 22.6 | 0.47 | 1 | 1 |
| | | 0.075 | 1.3 | 82.6 | 22.7 | 0.49 | 1 | 1 |
| Appl. Ex. 77 | quality improver of Ex. 4 | 0.030 | 1.6 | 82.3 | 22.8 | 0.51 | 1 | 1 |
| | | 0.075 | 1.2 | 82.0 | 22.6 | 0.52 | 1 | 1 |
| Appl. Ex. 78 | quality improver of Ex. 6 | 0.030 | 2.5 | 81.9 | 21.6 | 0.48 | 1 | 1 |
| | | 0.075 | 2.8 | 82.2 | 22.1 | 0.50 | 1 | 1 |
| Appl. Ex. 79 | quality improver of Ex. 7 | 0.030 | 2.9 | 81.4 | 21.3 | 0.53 | 1 | 1 |
| | | 0.075 | 3.5 | 81.5 | 21.6 | 0.56 | 1 | 1 |
| Appl. Ex. 80 | quality improver of Ex. 12 | 0.030 | 1.5 | 82.6 | 22.8 | 0.58 | 1 | 2 |
| | | 0.075 | 1.3 | 82.2 | 22.9 | 0.60 | 1 | 2 |
| Appl. Ex. 81 | quality improver of Ex. 14 | 0.030 | 2.8 | 81.9 | 21.2 | 0.51 | 2 | 1 |
| | | 0.075 | 3.0 | 82.2 | 21.6 | 0.53 | 3 | 1 |
| Appl. Ex. 82 | quality improver of Ex. 17 | 0.030 | 2.7 | 81.9 | 21.1 | 0.57 | 1 | 1 |
| | | 0.075 | 3.2 | 81.7 | 21.4 | 0.60 | 2 | 1 |
| Appl. Ex. 83 | quality improver of Ex. 18 | 0.030 | 3.0 | 81.2 | 21.2 | 0.59 | 1 | 2 |
| | | 0.075 | 3.1 | 81.0 | 21.2 | 0.61 | 1 | 2 |

TABLE 11

| | Quality improver used | Polyvalent metal (wt. %) | Incidence of fruit-cracking (%) | Degree of fruit coloring | Sugar content | Acidity | Dirt on a fruit surface | Phytotoxicity |
|---|---|---|---|---|---|---|---|---|
| Comp. Appl. Ex. 33 | quality improver of Comp. Ex. 1 | 0.030 | 9.7 | 80.2 | 20.4 | 0.60 | 4 | 1 |
| | | 0.075 | 9.4 | 80.5 | 20.8 | 0.63 | 5 | 1 |
| Comp. Appl. Ex. 34 | quality improver of Comp. Ex. 2 | 0.030 | 9.9 | 80.4 | 20.6 | 0.67 | 3 | 1 |
| | | 0.075 | 9.7 | 79.9 | 20.7 | 0.67 | 4 | 1 |
| Comp. Appl. Ex. 35 | quality improver of Comp. Ex. 3 | 0.030 | 11.7 | 79.3 | 20.1 | 0.63 | 3 | 1 |
| | | 0.075 | 11.6 | 79.5 | 20.0 | 0.60 | 3 | 1 |
| Comp. Appl. Ex. 36 | quality improver of Comp. Ex. 4 | 0.030 | 11.1 | 79.8 | 19.8 | 0.62 | 3 | 1 |
| | | 0.075 | 10.9 | 79.9 | 19.6 | 0.64 | 4 | 1 |
| Comp. Appl. Ex. 37 | calcium formate | 0.030 | 16.1 | 80.5 | 19.9 | 0.63 | 1 | 3 |
| | | 0.075 | 15.6 | 80.3 | 20.2 | 0.62 | 1 | 3 |
| Comp. Appl. Ex. 38 | preparation: $CaSO_4 \cdot 2H_2O$ 57%, $CaCl_2$ 27%, dispersing agent 16% | 0.030 | 15.3 | 80.1 | 20.4 | 0.61 | 1 | 2 |
| | | 0.075 | 14.9 | 79.9 | 20.6 | 0.64 | 1 | 2 |
| Comp. Appl. Ex. 39 | calcium chloride | 0.030 | 18.2 | 79.2 | 19.4 | 0.64 | 1 | 4 |
| | | 0.075 | 18.5 | 78.4 | 19.2 | 0.66 | 1 | 4 |
| Comp. Appl. Ex. 40 | water (control) | — | 24.1 | 78.8 | 19.1 | 0.67 | 1 | 1 |

Application Example 84

The effects of a quality improver in preventing sunburn were evaluated using an apple tree (Tsugaru).

That is, the quality improver of Example 1 was sprayed on the apple tree at the polyvalent metal concentrations shown in Table 12 over three times from early July (two-week interval). Each treatment was conducted on each branch by spraying with a backpack sprayer.

The evaluation was carried out on 50 randomly selected fruits. The incidence of sunburn was expressed as a ratio of the number of fruits with sunburn to the total number of fruits examined. The level of sunburn was expressed on a 4-point scale (none=0, mild=1, moderate=2, severe=3) based on a ratio of the sunburn area to the total surface area of the fruit. The fruit with a sunburn level of 2 or 3 was considered as a seriously damaged fruit. The dirt on a fruit surface was evaluated by a ratio of the surface area soiled whitish to the total surface area of the fruit on a scale of 1 to 5 (not soiled=1, slightly soiled=2, a little soiled=3, moderately soiled=4, much soiled=5). The phytotoxicity was evaluated on a scale of 1 to 5 (normal=1, slightly damaged=2, a little damaged=3, moderately damaged=4, much damaged=5). The results are shown in Table 12.

The quality improver of Example 1 was sprayed on the above apple tree at the polyvalent metal concentrations shown in Table 4 over four times from early June (two-week interval). Each treatment was conducted on each branch by spraying with a backpack sprayer.

Application Examples 85 to 93, Comparative Application Examples 41 to 44

The examinations were carried out in the same manner as in Application Example 84 except that the quality improvers of Examples 2 to 4, 6 to 7, 12, 14, 17 to 18, and Comparative Examples 1 to 4 were used instead of the quality improver of Example 1. The results are shown in Tables 12 and 13.

Comparative Application Example 45

The examination was carried out in the same manner as in Application Example 84 except that calcium formate was used instead of the quality improver of Example 1. The results are shown in Table 13.

Comparative Application Example 46

The examination was carried out in the same manner as in Application Example 84 except that the preparation containing 57% calcium sulfate dihydrate, 27% calcium chloride, and 16% dispersing agent etc. was used instead of the quality improver of Example 1. The results are shown in Table 13.

Comparative Application Example 47

The examination was carried out in the same manner as in Application Example 84 except that calcium chloride was used instead of the quality improver of Example 1. The results are shown in Table 13.

Comparative Application Example 48

The examination was carried out in the same manner as in Application Example 84 except that water (control) was used instead of the quality improver of Example 1. The results are shown in Table 13.

TABLE 12

| | Quality improver used | Polyvalent metal (wt. %) | Incidence of sunburn (%) | Seriously damaged fruit (%) | Dirt on a fruit surface | Phytotoxicity |
|---|---|---|---|---|---|---|
| Appl. Ex. 84 | quality improver of Ex. 1 | 0.030 | 2.0 | 0.0 | 1 | 1 |
| | | 0.075 | 0.0 | 0.0 | 1 | 1 |
| Appl. Ex. 85 | quality improver of Ex. 2 | 0.030 | 2.0 | 0.0 | 1 | 1 |
| | | 0.075 | 0.0 | 0.0 | 1 | 1 |

TABLE 12-continued

|  | Quality improver used | Polyvalent metal (wt. %) | Incidence of sunburn (%) | Seriously damaged fruit (%) | Dirt on a fruit surface | Phytotoxicity |
|---|---|---|---|---|---|---|
| Appl. Ex. 86 | quality improver of Ex. 3 | 0.030 | 2.0 | 0.0 | 1 | 1 |
|  |  | 0.075 | 0.0 | 0.0 | 1 | 1 |
| Appl. Ex. 87 | quality improver of Ex. 4 | 0.030 | 2.0 | 0.0 | 1 | 1 |
|  |  | 0.075 | 2.0 | 0.0 | 1 | 1 |
| Appl. Ex. 88 | quality improver of Ex. 6 | 0.030 | 2.0 | 0.0 | 1 | 1 |
|  |  | 0.075 | 2.0 | 2.0 | 1 | 1 |
| Appl. Ex. 89 | quality improver of Ex. 7 | 0.030 | 4.0 | 2.0 | 1 | 1 |
|  |  | 0.075 | 2.0 | 0.0 | 1 | 1 |
| Appl. Ex. 90 | quality improver of Ex. 12 | 0.030 | 2.0 | 0.0 | 1 | 2 |
|  |  | 0.075 | 0.0 | 0.0 | 1 | 2 |
| Appl. Ex. 91 | quality improver of Ex. 14 | 0.030 | 4.0 | 2.0 | 2 | 1 |
|  |  | 0.075 | 2.0 | 0.0 | 3 | 1 |
| Appl. Ex. 92 | quality improver of Ex. 17 | 0.030 | 2.0 | 0.0 | 1 | 1 |
|  |  | 0.075 | 2.0 | 2.0 | 2 | 1 |
| Appl. Ex. 93 | quality improver of Ex. 18 | 0.030 | 4.0 | 2.0 | 1 | 2 |
|  |  | 0.075 | 2.0 | 0.0 | 1 | 2 |

TABLE 13

|  | Quality improver used | Polyvalent metal (wt. %) | Incidence of sunburn (%) | Seriously damaged fruit (%) | Dirt on a fruit surface | Phytotoxicity |
|---|---|---|---|---|---|---|
| Comp. Appl. Ex. 41 | quality improver of Comp. Ex. 1 | 0.030 | 8.0 | 2.0 | 4 | 1 |
|  |  | 0.075 | 6.0 | 2.0 | 5 | 1 |
| Comp. Appl. Ex. 42 | quality improver of Comp. Ex. 2 | 0.030 | 8.0 | 4.0 | 3 | 1 |
|  |  | 0.075 | 8.0 | 2.0 | 4 | 1 |
| Comp. Appl. Ex. 43 | quality improver of Comp. Ex. 3 | 0.030 | 6.0 | 6.0 | 3 | 1 |
|  |  | 0.075 | 4.0 | 2.0 | 3 | 1 |
| Comp. Appl. Ex. 44 | quality improver of Comp. Ex. 4 | 0.030 | 6.0 | 4.0 | 3 | 1 |
|  |  | 0.075 | 6.0 | 4.0 | 4 | 1 |
| Comp. Appl. Ex. 45 | calcium formate | 0.030 | 10.0 | 6.0 | 1 | 3 |
|  |  | 0.075 | 10.0 | 6.0 | 1 | 3 |
| Comp. Appl. Ex. 46 | preparation: $CaSO_4 \cdot 2H_2O$ 57%, $CaCl_2$ 27%, dispersing agent 16% | 0.030 | 12.0 | 8.0 | 1 | 2 |
|  |  | 0.075 | 12.0 | 6.0 | 1 | 2 |
| Comp. Appl. Ex. 47 | calcium chloride | 0.030 | 10.0 | 8.0 | 1 | 4 |
|  |  | 0.075 | 12.0 | 8.0 | 1 | 4 |
| Comp. Appl. Ex. 48 | water (control) | — | 14.0 | 10.0 | 1 | 1 |

Application Example 94

The effects of a quality improver in reducing water core and improving fruit quality were evaluated using a pear tree (Housui).

That is, the quality improver of Example 1 was sprayed on the pear tree at the polyvalent metal concentrations shown in Table 14 over four times from late April (ten-day interval) and two times from middle July (ten-day interval). Each treatment was conducted on each branch by spraying with a backpack sprayer.

The evaluation was carried out on 30 randomly selected fruits. The degree of water core was evaluated by examining three cross sections of the stalk cavity part, the equatorial part, and the calyx end part of the fruit based on a 4-point scale (none=0, mild=1, moderate=2, severe=3). The result of the evaluation was expressed by the following equation: water core index={(1×the number of fruits with mild water core)+(2×the number of fruits with moderate water core)+(3×the number of fruits with severe water core)}/(the number of fruits examined). The fruit with a water core index of 2 or 3 was considered as a seriously damaged fruit. The ground color of fruit skin was determined using a color chart for Japanese pear based on a scale of 1 (immature) to 6 (overmature). The sugar content was determined using a sugar refractometer. The dirt on a fruit surface was evaluated by a ratio of the surface area soiled whitish to the total surface area of the fruit on a scale of 1 to 5 (not soiled=1, slightly soiled=2, a little soiled=3, moderately soiled=4, much soiled=5). The phytotoxicity was evaluated on a scale of 1 to 5 (normal=1, slightly damaged=2, a little damaged=3, moderately damaged=4, much damaged=5). The results are shown in Table 14.

Application Examples 95 to 103, Comparative Application Examples 49 to 52

The examinations were carried out in the same manner as in Application Example 94 except that the quality improvers of Examples 2 to 4, 6 to 7, 12, 14, 17 to 18, and Comparative Examples 1 to 4 were used instead of the quality improver of Example 1. The results are shown in Tables 14 and 15.

Comparative Application Example 53

The examination was carried out in the same manner as in Application Example 94 except that calcium formate was used instead of the quality improver of Example 1. The results are shown in Table 15.

Comparative Application Example 54

The examination was carried out in the same manner as in Application Example 94 except that the preparation containing 57% calcium sulfate dihydrate, 27% calcium chloride, and 16% dispersing agent etc. was used instead of the quality improver of Example 1. The results are shown in Table 15.

Comparative Application Example 55

The examination was carried out in the same manner as in Application Example 94 except that calcium chloride was used instead of the quality improver of Example 1. The results are shown in Table 15.

Comparative Application Example 56

The examination was carried out in the same manner as in Application Example 94 except that water (control) was used instead of the quality improver of Example 1. The results are shown in Table 15.

INDUSTRIAL APPLICABILITY

A sparingly water-soluble quality improver of the present invention prevents or reduces physiological disorders developed in various plants and further has the function of improving qualities of the plants, such as sugar content and acidity. In addition, the quality improver causes little fruit surface soiling to heighten the merchandise value, and it is lowly phytotoxic and highly safe.

The invention claimed is:

1. A particulate plant treatment composition containing a polyvalent metal, an organic acid having a carboxylic group, an alkali metal and/or ammonia, and phosphate ions and/or carbonate ions, and a particle size range of 0.01 μm ≦d50≦2.914 μm, which is for use as a leaf and fruit application to plants,
   wherein d50 is the 50% average particle diameter measured by dynamic light scattering.
2. The particulate plant treatment composition of claim 1, wherein molar ratios of organic acid having a carboxylic

TABLE 14

| | Quality improver used | Polyvalent metal (wt. %) | Water core index | Seriously damaged fruit (%) | Ground color | Sugar content | Dirt on a fruit surface | Phytotoxicity |
|---|---|---|---|---|---|---|---|---|
| Appl. Ex. 94 | quality improver of Ex. 1 | 0.030 | 0.30 | 6.7 | 4.0 | 14.0 | 1 | 1 |
| | | 0.075 | 0.27 | 3.3 | 4.1 | 14.1 | 1 | 1 |
| Appl. Ex. 95 | quality improver of Ex. 2 | 0.030 | 0.33 | 6.7 | 3.9 | 13.9 | 1 | 1 |
| | | 0.075 | 0.30 | 3.3 | 4.0 | 14.0 | 1 | 1 |
| Appl. Ex. 96 | quality improver of Ex. 3 | 0.030 | 0.33 | 6.7 | 3.9 | 14.0 | 1 | 1 |
| | | 0.075 | 0.33 | 6.7 | 3.9 | 14.0 | 1 | 1 |
| Appl. Ex. 97 | quality improver of Ex. 4 | 0.030 | 0.37 | 10.0 | 4.0 | 13.9 | 1 | 1 |
| | | 0.075 | 0.33 | 6.7 | 3.9 | 14.1 | 1 | 1 |
| Appl. Ex. 98 | quality improver of Ex. 6 | 0.030 | 0.40 | 10.0 | 3.8 | 13.8 | 1 | 1 |
| | | 0.075 | 0.37 | 6.7 | 4.0 | 14.0 | 1 | 1 |
| Appl. Ex. 99 | quality improver of Ex. 7 | 0.030 | 0.43 | 10.0 | 3.8 | 13.8 | 1 | 1 |
| | | 0.075 | 0.40 | 10.0 | 3.9 | 13.9 | 1 | 1 |
| Appl. Ex. 100 | quality improver of Ex. 12 | 0.030 | 0.33 | 6.7 | 4.0 | 14.1 | 1 | 2 |
| | | 0.075 | 0.30 | 6.7 | 4.1 | 14.2 | 1 | 2 |
| Appl. Ex. 101 | quality improver of Ex. 14 | 0.030 | 0.47 | 13.3 | 3.9 | 13.7 | 2 | 1 |
| | | 0.075 | 0.43 | 10.0 | 4.0 | 14.0 | 3 | 1 |
| Appl. Ex. 102 | quality improver of Ex. 17 | 0.030 | 0.43 | 10.0 | 3.9 | 13.9 | 1 | 1 |
| | | 0.075 | 0.37 | 6.7 | 4.0 | 13.8 | 2 | 1 |
| Appl. Ex. 103 | quality improver of Ex. 18 | 0.030 | 0.43 | 10.0 | 3.9 | 13.7 | 1 | 2 |
| | | 0.075 | 0.47 | 13.3 | 3.8 | 13.9 | 1 | 2 |

TABLE 15

| | Quality improver used | Polyvalent metal (wt. %) | Water core index | Seriously damaged fruit (%) | Ground color | Sugar content | Dirt on a fruit surface | Phytotoxicity |
|---|---|---|---|---|---|---|---|---|
| Comp. Appl. Ex. 49 | quality improver of Comp. Ex. 1 | 0.030 | 0.87 | 26.7 | 3.7 | 12.8 | 4 | 1 |
| | | 0.075 | 0.83 | 20.0 | 3.6 | 12.9 | 5 | 1 |
| Comp. Appl. Ex. 50 | quality improver of Comp. Ex. 2 | 0.030 | 0.87 | 23.3 | 3.7 | 13.1 | 4 | 1 |
| | | 0.075 | 0.80 | 20.0 | 3.7 | 13.3 | 4 | 1 |
| Comp. Appl. Ex. 51 | quality improver of Comp. Ex. 3 | 0.030 | 0.90 | 23.3 | 3.6 | 13.0 | 3 | 1 |
| | | 0.075 | 0.83 | 23.3 | 3.7 | 13.0 | 3 | 1 |
| Comp. Appl. Ex. 52 | quality improver of Comp. Ex. 4 | 0.030 | 0.87 | 23.3 | 3.6 | 12.7 | 3 | 1 |
| | | 0.075 | 0.87 | 23.3 | 3.6 | 12.9 | 4 | 1 |
| Comp. Appl. Ex. 53 | calcium formate | 0.030 | 0.80 | 23.3 | 3.6 | 13.0 | 1 | 3 |
| | | 0.075 | 0.77 | 16.7 | 3.8 | 13.2 | 1 | 3 |
| Comp. Appl. Ex. 54 | preparation: CaSO$_4$·2H$_2$O 57%, CaCl$_2$ 27%, dispersing agent 16% | 0.030 | 0.87 | 23.3 | 3.6 | 13.1 | 1 | 2 |
| | | 0.075 | 0.80 | 20.0 | 3.7 | 13.3 | 1 | 2 |
| Comp. Appl. Ex. 55 | calcium chloride | 0.030 | 0.97 | 30.0 | 3.7 | 12.8 | 1 | 4 |
| | | 0.075 | 0.90 | 26.7 | 3.5 | 12.6 | 1 | 4 |
| Comp. Appl. Ex. 56 | water (control) | — | 1.00 | 33.3 | 3.5 | 12.5 | 1 | 1 | group ions, alkali metal ions and/or ammonium ions, phosphate ions, carbonate ions to polyvalent metal ions are ranged as set forth below:

polyvalent metal ions/organic acid having a carboxylic group ions is 0.1 to 200,
polyvalent metal ions/alkali metal ions and/or ammonium ions is 0.03 to 200
polyvalent metal ions/phosphate ions is 1 to 10
polyvalent metal ions/carbonate ions is 0.6 to 10.

3. The particulate plant treatment composition of claim 1, wherein the polyvalent metal is at least one selected from the group consisting of calcium, magnesium and iron.

4. The particulate plant treatment composition of claim 1, wherein the below-mentioned equations a) and b) are satisfied:

$$0.01 \ \mu m \leq d50 \leq 1.5 \ \mu m \quad \text{a)}$$

$$0 \leq \alpha \leq 10; \quad \text{b)}$$

wherein $\alpha$ is $(d90-d10)/d50$,
d50 is the 50% average particle diameter measured by dynamic light scattering,
d90 is the 90% average particle diameter measured by dynamic light scattering, and
d10 is the 10% average particle diameter measured by dynamic light scattering.

5. The particulate plant treatment composition of claim 1, wherein the below-mentioned equations c) and d) are satisfied:

$$0.01 \ \mu m \leq d50 \leq 1.0 \ \mu m \quad \text{c)}$$

$$0 \leq \alpha \leq 8 \quad \text{d)}$$

wherein $\alpha$ is $(d90-d10)/d50$,
d50 is the 50% average particle diameter measured by dynamic light scattering
d90 is the 90% average particle diameter measured by dynamic light scattering,
and d10 is the 10% average particle diameter measured by dynamic light scattering.

6. The particulate plant treatment composition of claim 1, wherein the below-mentioned e) and f) are satisfied:

$$0.01 \ \mu m \leq d50 \leq 0.6 \ \mu m \quad \text{e)}$$

$$0 \leq \alpha \leq 5 \quad \text{f)}$$

wherein $\alpha$ is $(d90-d10)/d50$,
d50 is the 50% average particle diameter measured by dynamic light scattering
d90 is the 90% average particle diameter measured by dynamic light scattering,
and d10 is the 10% average particle diameter measured by dynamic light scattering.

7. A method of treating plants, comprising the step of:
applying the particulate plant treatment composition of claim 1 to a leaf or fruit of a plant.

* * * * *